United States Patent [19]

Von Deyn et al.

[11] Patent Number: 5,284,851
[45] Date of Patent: Feb. 8, 1994

[54] 1-ALKOXY-1,3-DIAZACYCLOALKANE DERIVATIVES AND THEIR USE AS PESTICIDES

[75] Inventors: Wolfgang Von Deyn, Neustadt; Albrecht Harreus, Ludwigshafen; Uwe Kardorff, Mannheim; Christoph Kuenast, Otterstadt, all of Fed. Rep. of Germany

[73] Assignee: BASF Aktiengesellschaft, Ludwigshafen, Fed. Rep. of Germany

[21] Appl. No.: 866,591

[22] Filed: Apr. 10, 1992

[30] Foreign Application Priority Data

Apr. 12, 1991 [DE] Fed. Rep. of Germany ....... 4111923

[51] Int. Cl.⁵ .................. A01N 43/50; A01N 43/54; C07D 233/02; C07D 239/06
[52] U.S. Cl. .................. 514/256; 514/385; 514/396; 514/398; 544/242; 544/335; 546/246; 548/300.1; 548/316.4; 548/324.5; 564/300; 564/301
[58] Field of Search ........... 544/335, 242; 548/300, 548/316.4, 324.5, 301.1; 514/385, 256, 396, 398; 564/300, 301; 546/246

[56] References Cited

U.S. PATENT DOCUMENTS

| | | | |
|---|---|---|---|
| 3,137,705 | 6/1964 | Prelog et al. | 564/301 X |
| 3,948,934 | 4/1976 | Tieman et al. | 548/300 X |
| 3,962,233 | 6/1976 | Roman et al. | 544/335 |
| 3,969,354 | 7/1976 | Tieman et al. | 548/300 X |
| 3,971,774 | 7/1976 | Tieman et al. | 548/300 X |
| 3,996,372 | 12/1976 | Kollmeyer | 548/300 X |
| 4,002,765 | 1/1977 | Tieman et al. | 548/300 X |
| 4,025,529 | 5/1977 | Kollmeyer | 548/300 |
| 4,029,791 | 6/1977 | Kollmeyer | 548/300 X |
| 4,033,952 | 7/1977 | Tieman et al. | 544/335 |
| 4,076,813 | 2/1978 | Roman et al. | 544/335 |
| 4,742,060 | 5/1988 | Shiokawa et al. | 514/252 |
| 4,968,695 | 11/1990 | Wolf et al. | 544/335 |

FOREIGN PATENT DOCUMENTS

| | | | |
|---|---|---|---|
| 2001988 | 1/1989 | Canada | 544/335 |
| 0390515 | 10/1990 | European Pat. Off. | 544/277 |
| 2709720 | 3/1977 | Fed. Rep. of Germany | 544/335 |
| 0549629 | 5/1974 | Switzerland | 534/607 |

OTHER PUBLICATIONS

Isowa et al I, Chemical Abstracts, vol. 80, #132724a (1974).
Isowa et al II, Chemical Abstracts, vol. 85, #32430m (1976).
Tetrahedron Lett. 27, 493 (1986).
J. Am. Chem. Soc. 80, 3339 (1950).
J. Heterocycl. Chem. 22, 937 (1985).
J. Heterocycl. Chem. 17, 1413 (1980).
Angew. Chem. 100, 591 (1967).
Pol J. Chem. 55(5), 1163 (1981).

*Primary Examiner*—Floyd D. Higel
*Attorney, Agent, or Firm*—Keil & Weinkauf

[57] ABSTRACT

1-Alkoxy-1,3-diazacycloalkane derivatives of the formula I

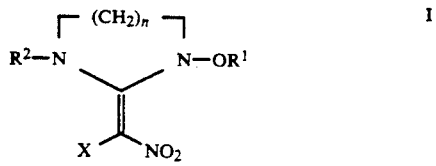

where:
n is 0 or 1;
$R^1$ is substituted or unsubstituted alkyl, alkylcarbonyl, cycloalkylcarbonyl, alkenyl or alkynyl, a substituted or unsubstituted heterocyclic radical or a group —C(=O)—R, where R is substituted or unsubstituted phenyl or a substituted or unsubstituted aliphatic or aromatic heterocyclic structure,
X is
  hydrogen; halogen; alkoxy; alkylthio; alkylcarbonyl; haloalkylcarbonyl; alkoxycarbonyl;
  substituted or unsubstituted alkyl, phenyl, phenoxy, phenylthio, benzoyl or phenyloxycarbonyl; and
$R^2$ is
  hydrogen or alkyl,
processes and intermediates for their manufacture, and their use in pesticides.

12 Claims, No Drawings

1-ALKOXY-1,3-DIAZACYCLOALKANE DERIVATIVES AND THEIR USE AS PESTICIDES

The present invention relates to 1-alkoxy-1,3-diazacycloalkane derivatives of the general formula I

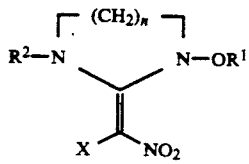

where
n is 0 or 1;
$R^1$ is $C_1$-$C_{10}$-alkyl, $C_1$-$C_6$-alkylcarbonyl, $C_3$-$C_6$-cycloalkylcarbonyl, $C_3$-$C_6$-alkenyl or $C_3$-$C_6$-alkynyl, where these groups may carry from one to five halogen atoms and/or one or two of the following radicals:
$C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylamino, $C_1$-$C_6$-dialkylamino, $C_1$-$C_4$-alkylcarbonyl, $C_3$-$C_6$-cycloalkylcarbonyl, $C_1$-$C_4$-alkylcarbonyloxy or $C_3$-$C_6$-cycloalkylcarbonyloxy,
phenylcarbonyl, phenylcarbonyloxy, phenyl, phenoxy or phenylthio, where the phenyl radicals in turn may carry from one to five halogen atoms and/or from one to three of the following groups: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio;
a 5-membered or 6-membered heterocyclic, aliphatic or aromatic radical containing from one to three hetero atoms selected from the group consisting of oxygen, sulfur and nitrogen, where this radical may carry one or two of the following substituents: halogen, $C_1$-$C_4$-alkyl, $C_3$-$C_6$-cycloalkyl, $C_1$-$C_4$-alkoxy and phenyl, where the phenyl radicals in turn may carry from one to five halogen atoms and/or from one to three of the following groups: cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;
or —C(=O)—R, where
R is phenyl or a 5-membered or 6-membered heterocyclic, aliphatic or aromatic radical which contains from one to three hetero atoms selected from the group consisting of oxygen, sulfur and nitrogen, where the radicals may carry one or two of the following substituents: cyano, nitro, halogen, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio and phenyl;
X is
hydrogen; halogen, $C_1$-$C_4$-alkoxy; $C_1$-$C_4$-alkylthio; $C_1$-$C_6$-alkylcarbonyl; $C_1$-$C_6$-haloalkylcarbonyl; $C_1$-$C_6$-alkoxycarbonyl;
$C_1$-$C_4$-alkyl which may carry from one to nine halogen atoms and/or from one to three of the following groups: hydroxyl, $C_1$-$C_4$-alkoxy, $C_1$-$C_4$-alkylthio, phenoxy and phenylthio;
phenyl, phenoxy, phenylthio, benzoyl or phenyloxycarbonyl, where the phenyl radicals in turn may carry from one to five halogen atoms and/or from one to three of the following groups: cyano, nitro, $C_1$-$C_4$-alkyl and $C_1$-$C_4$-alkoxy; and
$R^2$ is hydrogen or $C_1$-$C_4$-alkyl.

The present invention furthermore relates to a process and intermediates for the preparation of the compounds I, pesticides containing them and methods for pest control.

The compounds of the general formula I may occur in various tautomeric and isomeric forms, which likewise form a subject of the invention.

DE-A 24 45 421 discloses 2-(nitromethylene)-1,3-diazacycloalkanes (for example hexahydro-1-methyl-2-(nitromethylene)pyrimidine) having insecticidal activity.

The level of activity or duration of activity of these compounds described above is, however, not always satisfactory.

It is an object of the present invention to provide novel 1-alkoxy-1,3-diazacycloalkane derivatives having improved activity.

We have found that this object is achieved by the 1-alkoxy-1,3-diazacycloalkane derivatives of the general formula I which are defined at the outset, and a process and intermediates for their preparation. We have also found that the compounds I are very useful for controlling pests.

The compounds I are obtained by reacting a 1-alkoxyamino-2- or -3-aminoalkane of the general formula II in a conventional manner (J. Heterocycl. Chem. 22 (1985), 937) with a 1,1-bisalkylthioalkene of the general formula III in an organic solvent.

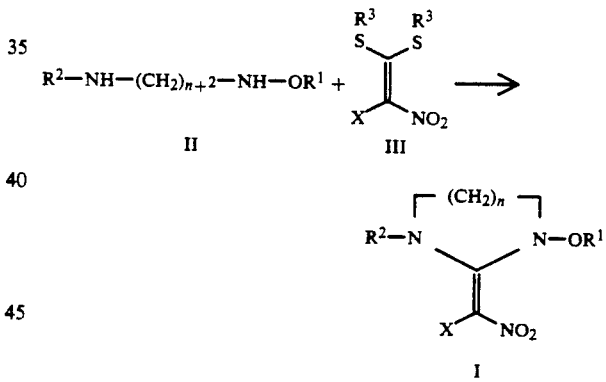

In formula III, $R^3$ is alkyl, preferably $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $C_1$-$C_4$-alkyl, such as methyl, ethyl, propyl, 1-methylethyl, butyl, 1-methylpropyl, 2-methylpropyl or 1,1-dimethylethyl, or benzyl.

The reaction is usually carried out at from 0° to 180° C., preferably from 20° to 140° C.

Suitable inert organic solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole or tetrahydrofuran, nitriles, such as acetonitrile or propionitrile, ketones, such as acetone, methyl ethyl ketone, diethyl ketone or tert-butyl methyl ketone, alcohols, such as methanol, ethanol, n-propanol, isopropanol, n-butanol or tert-butanol, and dimethyl sulfoxide and dimethylformamide, particularly preferably ethanol, n-propanol or isopropanol.

It is also possible to use mixtures of the stated solvents.

The starting materials are usually reacted with one another in stoichiometric amounts. It may be advantageous, for example in order to increase the yield, to use one of the starting materials in an excess of from 0.1 to 10, preferably from 0.2 to 1.5, mole equivalents.

The compounds of the general formula I in which $R^2$ is $C_1$-$C_4$-alkyl are advantageously obtained by reacting a 1-alkoxy-1,3-diazacycloalkane of the general formula Ia with a compound of the general formula V.

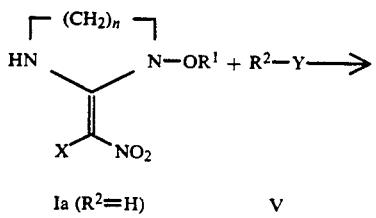

Ia ($R^2$=H)     V

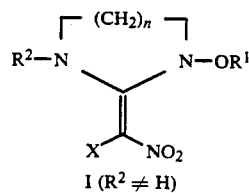

I ($R^2 \neq$ H)

In formula V, Y is a nucleofugic leaving group, such as halogen, for example fluorine, chlorine, bromine or iodine, preferably chlorine or bromine, or a radical of sulfonic acid, such as methanesulfonyl, trifluoromethylsulfonyl, phenylsulfonyl or p-toluenesulfonyl, preferably methanesulfonyl.

The reaction is usually carried out at from $-10°$ to $150°$ C., preferably from $0°$ to $100°$ C., in an inert organic solvent in the presence of a base.

Suitable inert organic solvents are aliphatic hydrocarbons, such as pentane, hexane, cyclohexane or petroleum ether, aromatic hydrocarbons, such as toluene, o-, m- or p-xylene, halohydrocarbons, such as methylene chloride, chloroform or chlorobenzene, ethers, such as diethyl ether, diisopropyl ether, tert-butyl methyl ether, dioxane, anisole or tetrahydrofuran, nitriles, such as acetonitrile or propionitrile, ketones, such as acetone, methyl ethyl ketone, diethyl ketone or tert-butyl methyl ketone, alcohols, such as methanol, ethanol, n-propanol, isopropanol, n-butanol or tert-butanol, and dimethyl sulfoxide and dimethylformamide, particularly preferably methylene chloride, dimethyl sulfoxide or dimethylformamide.

It is also possible to use mixtures of the stated solvents.

Suitable bases are generally inorganic compounds, such as alkali metal and alkaline earth metal hydroxides, e.g. lithium hydroxide, sodium hydroxide, potassium hydroxide or calcium hydroxide, alkali metal and alkaline earth metal oxides, such as lithium oxide, sodium oxide, calcium oxide or magnesium oxide, alkali metal and alkaline earth metal hydrides, such as lithium hydride, sodium hydride, potassium hydride or calcium hydride, alkali metal amides, such as lithium amide, sodium amide or potassium amide, alkali metal and alkaline earth metal carbonates, such as lithium carbonate, sodium carbonate, potassium carbonate or calcium carbonate, and alkali metal bicarbonates, such as sodium bicarbonate, organometallic compounds, in particular alkali metal alkyls, such as methyllithium, butyllithium or phenyllithium, alkylmagnesium halides, such as methylmagnesium chloride, and alkali metal and alkaline earth metal alcoholates, such as sodium methylate, sodium ethylate, potassium ethylate or potassium tert-butylate, and dimethoxy-magnesium, as well as organic bases, for example tertiary amines, such as trimethylamine, triethylamine, triisopropylethylamine, and N-methylpiperidine, pyridine, substituted pyridines, such as collidine, lutidine or 4-dimethylaminopyridine, and bicyclic amines.

Sodium hydroxide, potassium hydroxide, sodium carbonate, potassium carbonate, sodium hydride and potassium tert-butylate are particularly preferred.

The bases are used in general in equimolar amounts, but may also be used in excess or, if necessary, as solvents.

The starting materials are usually reacted with one another in stoichiometric amounts. It may be advantageous, for example in order to increase the yield, to use one of the starting materials in an excess of from 0.1 to 10, preferably from 0.2 to 1.5, mole equivalents.

The compounds I in which $R^2$ is hydrogen and X is alkylcarbonyl, alkoxycarbonyl, benzoyl or phenoxycarbonyl, are advantageously obtained by reacting a 1-alkoxy-1,3-diaza-2-methylthiocycloalkane derivative of the general formula VII in a conventional manner (J. Heterocyclic Chem. 17 (1980), 1413) with a nitrocarbonyl compound of the general formula VIII in the presence or absence of a catalyst.

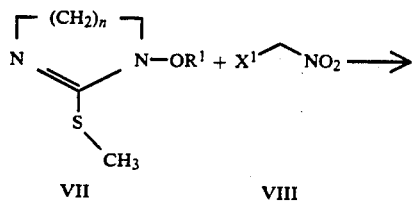

VII     VIII

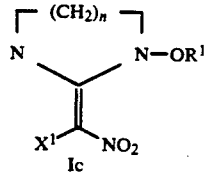

Ic

In formulae VIII and Ic, $X^1$ is $C_1$-$C_6$-alkylcarbonyl, preferably methylcarbonyl or ethylcarbonyl, $C_1$-$C_6$-alkoxycarbonyl, preferably methoxycarbonyl or ethoxycarbonyl, phenylcarbonyl or phenoxycarbonyl.

The reaction is usually carried out at from $20°$ to $180°$ C., preferably from $50°$ to $150°$ C.

Suitable catalysts are in general Lewis acids, such as boron trifluoride, titanium tetrachloride, aluminum trichloride or zinc chloride, particularly preferably zinc chloride.

The starting materials are usually reacted with one another in stoichiometric amounts. It may be advantageous, for example in order to increase the yield, to use one of the starting materials in an excess of from 0.1 to 10, preferably from 0.2 to 1.5, mole equivalents.

The 1-alkoxy,1,3-diaza-2-methylthiocycloalkane derivatives of the general formula VII required for the reaction can be prepared by generally known chemical processes (J. Am. Chem. Soc. 80 (1950), 3339) from the 1-alkoxyamino-2- or -3-aminoalkanes of the general formula II.

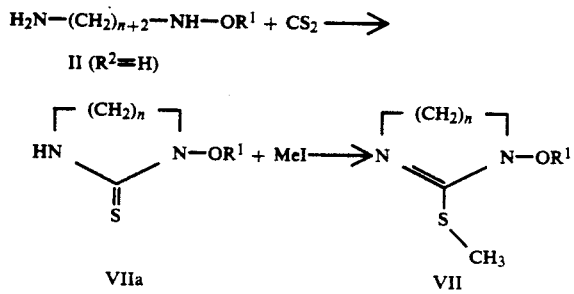

The nitroalkyl compounds of the general formula VIII are known or can be prepared by known methods (Tetrahedron Lett. 27 (1986), 493).

Furthermore, other compounds of the general formula I where R² is hydrogen are advantageously obtained in a conventional manner from 1-alkoxy-1,3-diazacycloalkanes of the general formula Ib by substitution of the α-carbon atoms of the nitromethylene group.

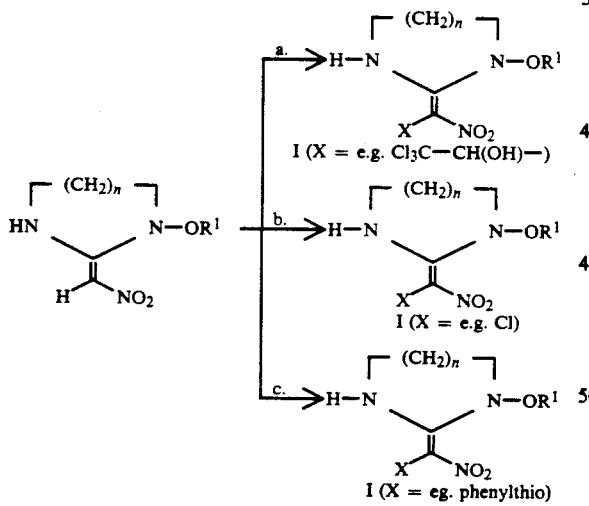

a. For example, active aldehydes, such as formaldehyde or chloral, can be subjected to an addition reaction at the α-carbon of the nitromethylene group (US-A 4,033,952 and EP-A 292 822).

b. In addition, the alpha-carbon atom can also be halogenated by halogenating agents, such as N-chlorosuccinimide, N-bromosuccinimide and halogen itself (US-A 3,962,233).

c. Furthermore, the alpha-carbon atom of the nitromethylene group can be acylated or sulfinylated (US-A 4,076,813 and US-A 3,969,354).

The 1-alkoxyamino-2-aminoalkanes of the general formula II which are required for the synthesis of the compounds I in which n is 0 are known or can be prepared by known methods (DE-A 27 09 720).

For example, the preparation of such 1-alkoxyamino-ω-aminoalkanes of the general formula II where R¹ is substituted benzyl is described in Pol. J. Chem. 55(5) (1981), 1163–1167.

1-Alkoxyamino-3-aminoalkanes of the general formula IIa are novel and form a subject of the present invention.

These novel intermediates are obtained by reacting an alkylamine of the general formula IIb in a conventional manner with a hydroxylamine of the general formula IV in an inert organic solvent and then eliminating the protective group.

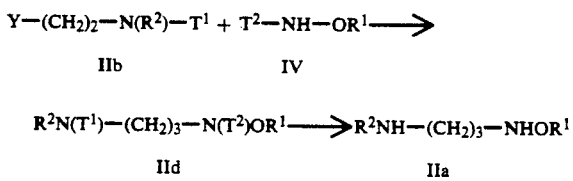

In formula IIb, Y is a leaving group, such as a sulfonic acid radical or halogen. Among the sulfonic acid radicals, methanesulfonyl, trifluoromethanesulfonyl, benzene-sulfonyl and p-toluenesulfonyl are preferred, while preferred halogen atoms are chlorine or bromine.

In formula IV, T² is hydrogen or a protective group for amino functions and T¹ is a protective group for amino functions, as described in, for example, T. W. Greene, Protective Groups in Organic Synthesis, Chapter 7, Wiley, 1981, particularly preferred protective groups being methoxycarbonyl, ethoxycarbonyl, tert-butoxycarbonyl, 2,2,2-trichloroethoxycarbonyl and benzyloxycarbonyl.

Furthermore, the intermediates of the general formula IIa where R² is hydrogen are obtained by reacting an alkylamine of the general formula IIe' with a hydroxylamine of the general formula IV as stated above.

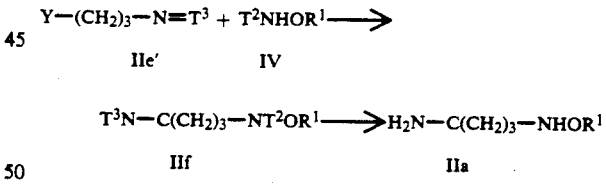

In the formula IIe', T³ is a bidentate, cyclic protective group for amino functions, for example the phthalimido group.

This reaction is usually carried out at from −20° to 180° C., preferably from 0° to 120° C.

Suitable solvents are aliphatic hydrocarbons, such as pentane, hexane, cyclohexane or petroleum ether, aromatic hydrocarbons, such as toluene, o-, m- or p-xylene, halohydrocarbons, such as methylene chloride, chloroform or chlorobenzene, ethers, such as diethyl ether, diisopropyl ether, tert-butyl methyl ether, dioxane, anisole or tetrahydrofuran, nitriles, such as acetonitrile or propionitrile, ketones, such as acetone, methyl ethyl ketone, diethyl ketone or tert-butyl methyl ketone, alcohols, such as methanol, ethanol, n-propanol, isopropanol, n-butanol or tert-butanol, and dimethyl sulfoxide and dimethylformamide, particularly preferably methanol, ethanol, n-propanol, isopropanol, n-butanol, tetrahydrofuran or dimethylformamide.

It is also possible to use mixtures of the stated solvents.

Suitable bases are generally inorganic compounds, such as alkali metal and alkaline earth metal hydroxides, e.g. lithium hydroxide, sodium hydroxide, potassium hydroxide or calcium hydroxide, alkali metal and alkaline earth metal oxides, such as lithium oxide, sodium oxide, calcium oxide or magnesium oxide, alkali metal and alkaline earth metal hydrides, such as lithium hydride, sodium hydride, potassium hydride or calcium hydride, alkali metal amides, such as lithium amide, sodium amide or potassium amide, alkali metal and alkaline earth metal carbonates, such as lithium carbonate, sodium carbonate, potassium carbonate or calcium carbonate, and alkali metal bicarbonates, such as sodium bicarbonate, organometallic compounds, in particular alkali metal alkyls, such as methyllithium, butyllithium or phenyllithium, alkylmagnesium halides, such as methylmagnesium chloride, and alkali metal and alkaline earth metal alcoholates, such as sodium methylate, sodium ethylate, potassium ethylate or potassium tert-butylate, and dimethoxymagnesium, as well as organic bases, for example tertiary amines, such as trimethylamine, triethylamine, triisopropylethylamine, and N-methylpiperidine, pyridine, substituted pyridines, such as collidine, lutidine or 4-dimethylaminopyridine, and bicyclic amines.

Sodium hydroxide, potassium hydroxide, sodium bicarbonate, sodium hydride and potassium tert-butylate are particularly preferred.

The educts are generally reacted with one another in equimolar amounts. It may be advantageous, for example in order to increase the yield, to use one of the starting materials in an excess of from 0.1 to 10, preferably from 0.2 to 1.5, mole equivalents.

The novel intermediates IIa are also obtained, for example, by reacting a 1-amino-3-hydroxyaminopropane of the general formula IIc in a conventional manner with an alkylating agent of the general formula VI in an inert organic solvent in the presence of a base.

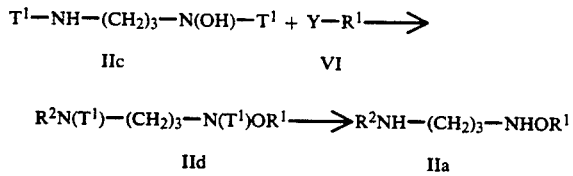

$$T^1-NH-(CH_2)_3-N(OH)-T^1 + Y-R^1 \longrightarrow$$

IIc          VI $$R^2N(T^1)-(CH_2)_3-N(T^1)OR^1 \longrightarrow R^2NH-(CH_2)_3-NHOR^1$$

IId          IIa

In the formula IIc, $T^1$ has, in general and in particular, the abovementioned meanings.

In the formula VI, Y is a nucleofugic leaving group, as stated above in general and in particular for formula IIb.

The reaction is usually carried out at from $-20°$ to $180°$ C., preferably from $0°$ to $120°$ C.

Suitable solvents are aliphatic hydrocarbons, such as pentane, hexane, cyclohexane or petroleum ether, aromatic hydrocarbons, such as toluene, o-, m- or p-xylene, halohydrocarbons, such as methylene chloride, chloroform or chlorobenzene, ethers, such as diethyl ether, diisopropyl ether, tert-butyl methyl ether, dioxane, anisole or tetrahydrofuran, nitriles, such as acetonitrile or propionitrile, ketones, such as acetone, methyl ethyl ketone, diethyl ketone or tert-butyl methyl ketone, alcohols, such as methanol, ethanol, n-propanol, isopropanol, n-butanol or tert-butanol, and dimethyl sulfoxide and dimethylformamide, particularly preferably toluene, tetrahydrofuran or dimethylformamide.

It is also possible to use mixtures of the stated solvents.

Suitable bases are generally inorganic compounds, such as alkali metal and alkaline earth metal hydroxides, e.g. lithium hydroxide, sodium hydroxide, potassium hydroxide or calcium hydroxide, alkali metal and alkaline earth metal oxides, such as lithium oxide, sodium oxide, calcium oxide or magnesium oxide, alkali metal and alkaline earth metal hydrides, such as lithium hydride, sodium hydride, potassium hydride or calcium hydride, alkali metal amides, such as lithium amide, sodium amide or potassium amide, alkali metal and alkaline earth metal carbonates, such as lithium carbonate, sodium carbonate, potassium carbonate or calcium carbonate, and alkali metal bicarbonates, such as sodium bicarbonate, organometallic compounds, in particular alkali metal alkyls, such as methyllithium, butyllithium or phenyllithium, alkylmagnesium halides, such as methylmagnesium chloride, and alkali metal and alkaline earth metal alcoholates, such as sodium methylate, sodium ethylate, potassium ethylate or potassium tert-butylate, and dimethoxymagnesium, as well as organic bases, for example tertiary amines, such as trimethylamine, triethylamine, triisopropylethylamine, and N-methylpiperidine, pyridine, substituted pyridines, such as collidine, lutidine or 4-dimethylaminopyridine, and bicyclic amines.

Sodium hydroxide, potassium hydroxide, sodium bicarbonate, sodium hydride and potassium tert-butylate are particularly preferred.

The educts are generally reacted with one another in general in equimolar amounts. It may be advantageous, for example in order to increase the yield, to use one of the starting materials in an excess of from 0.1 to 10, preferably from 0.2 to 1.5, mole equivalents.

1-Amino-3-hydroxyaminopropane dihydrochloride is described in Biochemistry 10 (1971), 4894.

The protective groups are eliminated by the methods stated in Greene (Protective Groups in Organic Synthesis, Chapter 7, Wiley (1981)).

Some of the 1,1-bisalkylthioalkenes of the formula III are described in Angew. Chem. 100 (1967), 591–604 or can be prepared by the methods described there.

If the compounds of the formula II are used in the form of their acid addition salts, the reaction is advantageously carried out with the addition of an acid acceptor. Usually, not less than equivalent amounts of the acid acceptor are used, but the latter may also be employed in excess or, if necessary, as a solvent.

Examples of suitable acid acceptors are hydroxides of alkali metals and alkaline earth metals, such as sodium hydroxide, potassium hydroxide or calcium hydroxide, alcoholates of alkali and alkaline earth metals, such as sodium methylate, sodium ethylate, calcium methylate or potassium tert-butylate, alkali metal or alkaline earth metal hydrides, such as sodium hydride, potassium hydride or calcium hydride, alkali metal and alkaline earth metal carbonates, such as sodium carbonate, potassium carbonate or calcium carbonate, and aliphatic, aromatic or heterocyclic amines, such as dimethylamine, triethylamine, diisopropylamine, piperidine, piperazine, pyrrolidine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), pyridine or pyrrole.

The hydroxylamine derivatives IV which are required for the reaction and in which $T^2$ is hydrogen are known or can be prepared by known methods (DE-A 38 38 310).

The alkyl derivatives of the formulae V and VI which are required for the reaction are known or are commercially available or can be prepared by generally known chemical processes.

In view of the intended use of the alkoxy-1,3-diazacycloalkane derivatives of the general formula I, suitable substituents are the following radicals:

$R^1$ is $C_1$–$C_{10}$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular $C_1$–$C_4$-alkyl;

$C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably $C_1$–$C_4$-alkylcarbonyl, in particular $C_1$- or $C_2$-alkylcarbonyl;

$C_3$–$C_6$-cycloalkylcarbonyl, such as cyclopropylcarbonyl, cyclobutylcarbonyl, cyclopentylcarbonyl or cyclohexylcarbonyl, preferably cyclopropylcarbonyl, cyclopentylcarbonyl or cyclohexylcarbonyl;

$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl or 2-butenyl; or $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl;

where these groups may carry from one to five halogen atoms, such as fluorine, chlorine, bromine or iodine, preferably fluorine, chlorine or bromine, in particular fluorine or chlorine, and/or one or two of the following radicals:

$C_3$–$C_6$-cycloalkyl, such as cyclopropyl, cyclobutyl, cyclopentyl, cyclohexyl, cycloheptyl or cyclooctyl, in particular cyclopropyl or cyclohexyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular $C_1$- or $C_2$-alkoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular 2,2,2-trifluoroethoxy or 2-chloro-2,2-difluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trichloromethylthio;

$C_1$–$C_6$-alkylamino, such as methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylproylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino, in particular $C_1$- or $C_2$-alkylamino;

di-$C_1$–$C_6$-alkylamino, in particular di-$C_1$–$C_4$-alkylamino, such as N,N-dimethylamino, N,N-diethylamino, N,N-dipropylamino, N,N-di-(1-methylethyl)-amino, N,N-dibutylamino, N,N-di-(1-methylpropyl)-amino, N,N-di-(2-methylpropyl)-amino, N,N-di-(1,1-dimethylethyl)-amino, N-ethyl-N-methylamino, N-methyl-N-propylamino, N-methyl-N-(1-methylethyl)-amino, N-butyl-N-methylamino, N-methyl-N-(1-methylpropyl)-amino, N-methyl-N-(2-methylpropyl)-amino, N-(1,1-dimethylethyl)-N-methylamino, N-ethyl-N-propylamino, N-ethyl-N-(1-methylethyl)-amino, N-butyl-N-ethylamino, N-ethyl-N-(1-methylpropyl)-amino, N-ethyl-N-(2-methylpropyl)-amino, N-ethyl-N-(1,1-dimethylethyl)-amino, N-(1-methylethyl)-N-propylamino, N-butyl-N-propylamino, N-(1-methylpropyl)-N-propylamino, N-(2-methylpropyzl)-N-propylamino, N-(1,1-dimethylethyl)-N-propylamino, N-butyl-N-(1-methylethyl)-amino, N-(1-methylethyl)-N-(1-methylpropyl)-amino, N-(1-methylethyl)-N-(2-methylpropyl)-amino, N-(1,1-dimethylethyl)-N-(1-methylethyl)-amino, N-butyl-N-(1-methylpropyl)-amino, N-butyl-N-(2-methylpropyl)-amino, N-butyl-N-(1,1-dimethylethyl)-amino, N-(1-methylpropyl)-N-(2-methylpropyl)-amino, N-(1,1-dimethylethyl)-N-(1-methylpropyl)-amino or N-(1,1-dimethylethyl)-N-(2-methylpropyl)-amino, in particular N,N-dimethylamino or N,N-diethylamino;

$C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably $C_1$–$C_4$-alkylcarbonyl, in particular $C_1$- or $C_2$-alkylcarbonyl;

$C_3$–$C_6$-cycloalkylcarbonyl, such as cyclopropylcarbonyl, cyclobutylcarbonyl, cyclopentylcarbonyl or cyclohexylcarbonyl, preferably cyclopropylcarbonyl, cyclopentylcarbonyl or cyclohexylcarbonyl;

$C_1$–$C_6$-alkylcarbonyloxy such as methylcarbonyloxy, ethylcarbonyloxy, propylcarbonyloxy, 1-methylethylcarbonyloxy, butylcarbonyloxy, 1-methylpropylcarbonyloxy, 2-methylpropylcarbonyloxy, 1,1-dimethylethylcarbonyloxy, pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, hexylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy or 1-ethyl-2-methylpropylcarbonyloxy, preferably $C_1$–$C_4$-alkylcarbonyloxy, in particular $C_1$- or $C_2$-alkylcarbonyloxy;

$C_3$–$C_6$-cycloalkylcarbonyloxy such as cyclopropylcarbonyloxy, cyclobutylcarbonyloxy, cyclopentylcarbonyloxy or cyclohexylcarbonyloxy, preferably cyclopropylcarbonyloxy, cyclopentylcarbonyloxy or cyclohexylcarbonyloxy;

phenylcarbonyl, phenylcarbonyloxy, phenyl, phenoxy or phenylthio, where the phenyl radicals in turn may carry from one to five halogen atoms, such as fluorine, chlorine, bromine or iodine, in particular fluorine or chlorine, and/or from one to three of the following groups:

cyano, nitro, $C_1$–$C_4$-alkyl, such as methyl, ethyl, propyl, 1-methylethyl, butyl, 1-methylpropyl, 2-methylpropyl or 1,1-dimethylethyl, in particular methyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular $C_1$- or $C_2$-alkoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2-trichloroethylthio or pentafluoroethylthio, in particular trichloromethylthio or trifluoromethylthio;

a 5-membered or 6-membered heterocyclic, aliphatic or aromatic radical containing from one to three hetero atoms selected from the group consisting of oxygen, sulfur and nitrogen, for example heteroaromatics having a five-membered ring and containing from one to three nitrogen atoms and/or an oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl or 1,3,4-triazol-2-yl, preferably 5-isoxazolyl, 2-thienyl and 5-pyrazolyl, in particular 5-thiazolyl or 5-isoxazolyl;

heteroaromatics having a six-membered ring and containing from one to three nitrogen atoms as hetero atoms, such as 2-pyridyl, 2-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl, in particular 5-pyrimidinyl, 2-pyridyl or 3-pyridyl;

5-membered or 6-membered, saturated or partially unsaturated heterocyclic structures containing from one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxodiazolidin-3-yl, 1,2,4-oxadiazolidin-5-yl, 1,2,4-thiadiazolidin-3-yl, 1,2,4-thiadiazolidin-5-yl, 1,2,4-thiadiazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol- 4-yl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3-dioxolan-2-yl, 1,3-dioxolan-4-yl, 1,3-dioxan-5-yl, 1,4-dioxan-2-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl or 1,2,4-tetrahydrotriazin-3-yl, in particular 2-tetrahydrofuranyl, 1,3-dioxolan-2-yl or 1,3-dioxan-2-yl, where these radicals may carry one or two of the following substituents: halogen, such as fluorine, chlorine, bromine or iodine, in particular fluorine or chlorine; $C_1$–$C_4$-alkyl, such as methyl, ethyl, propyl, 1-methylethyl, butyl, 1-methylpropyl, 2-methylpropyl or 1,1-dimethylethyl, in particular $C_1$- or $C_2$-alkyl;

$C_3$–$C_6$-cycloalkyl, such as cyclopropyl, cyclobutyl, cyclopentyl or cyclohexyl, preferably cyclopropyl, cyclopentyl or cyclohexyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, in particular $C_1$- or $C_2$-alkoxy;

and phenyl, where the phenyl radicals in turn may carry from one to five halogen atoms, such as fluorine, chlorine, bromine or iodine, preferably fluorine or chlorine, and/or from one to three of the following groups: cyano, nitro, $C_1$–$C_4$-alkyl, such as methyl, ethyl, propyl, 1-methylethyl, butyl, 1-methylpropyl, 2-methylpropyl or 1,1-dimethylethyl, preferably $C_1$- or $C_2$-alkyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably difluoromethyl or trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably $C_1$- or $C_2$-alkoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably difluoromethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably $C_1$- or $C_2$-alkylthio; and $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2, 2, 2 -trichloroethylthio or pentafluoroethylthio;

or —C(=O)—R, where

R is phenyl or one of the five-membered or six-membered heterocyclic, aliphatic or aromatic radicals which are stated in general and in particular above and contain from one to three hetero atoms selected from the group consisting of oxygen, sulfur and nitrogen, where these radicals may carry one or two of the following substituents: cyano, nitro or halogen, such as fluorine, chlorine, bromine or iodine, preferably fluorine or chlorine;

$C_1$–$C_4$-alkyl, such as methyl, ethyl, propyl, 1-methylethyl, butyl, 1-methylpropyl, 2-methylpropyl or 1,1-dimethylethyl, preferably $C_1$- or $C_2$-alkyl, $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably difluoromethyl or trifluoromethyl, $C_1$–$C_4$-alkoxy, such as methoxy, ethoxy, propoxy, 1-methylethoxy, butoxy, 1-methylpropoxy, 2-methylpropoxy or 1,1-dimethylethoxy, preferably $C_1$- or $C_2$-alkoxy, $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably difluoromethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, preferably $C_1$- or $C_2$-alkylthio;

$C_1$–$C_4$-haloalkylthio, in paticular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, or phenyl;

X is hydrogen, halogen, such as fluorine, chlorine, bromine or iodine, in particular chlorine or bromine;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

$C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular $C_1$- or $C_2$-alkylcarbonyl;

$C_1$–$C_6$-haloalkylcarbonyl, in particular $C_1$- or $C_2$-haloalkylcarbonyl, such as chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl or pentafluoroethylcarbonyl, in particular trichloromethylcarbonyl or trifluoromethylcarbonyl;

$C_1$–$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentyloxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1, 2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropxycarbonyl or 1-ethyl-2-methylpropoxycarbonyl, preferably $C_1$- or $C_2$-alkoxycarbonyl;

$C_1$–$C_4$-alkyl, such as methyl, ethyl, propyl, 1-methylethyl, butyl, 1-methylpropyl, 2-methylpropyl or 1,1-dimethylethyl, preferably $C_1$- or $C_2$-alkyl, which may carry from one to nine halogen atoms, such as fluorine, chlorine, bromine or iodine, preferably fluorine or chlorine, and/or from one to three of the following groups: hydroxyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular $C_1$ or $C_2$-alkoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

phenoxy or phenylthio;

phenyl, phenoxy, phenylthio, benzoyl or phenoxycarbonyl, where the phenyl radicals in turn may carry from one to five halogen atoms, such as fluorine, chlorine, bromine or iodine, in particular fluorine or chlorine, and/or from one to three of the following groups:

cyano, nitro, $C_1$–$C_4$-alkyl, such as methyl, ethyl, propyl, 1-methylethyl, butyl, 1-methylpropyl, 2-methylpropyl or 1,1-dimethylethyl, in particular $C_1$- or $C_2$-alkyl, or $C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, and $R^2$ is hydrogen or $C_1$–$C_4$-alkyl, such as methyl, ethyl, propyl, 1-methylethyl, butyl, 1-methylpropyl, 2-methylpropyl or 1,1-dimethylethyl, preferably methyl.

n is 0 or 1.

Other preferred 1-alkoxy-1,3-diazacycloalkane derivatives of the general formula I are those in which n is 1 and X nd $R^2$ are each hydrogen.

In view of the intended use of the 1-alkoxyamino-3-aminoalkane derivatives of the general formula IIa as intermediates, suitable substituents are the following radicals:

$R^1$ is

C₁–C₆-alkyl as stated above in general and in particular, and these groups may carry from one to five halogen atoms as stated above in general and in particular and/or one or two of the following radicals stated above in general and in particular: C₃–C₆-cycloalkyl, C₁–C₄-alkoxy, C₁–C₄-haloalkoxy, C₁–C₄-alkylthio, C₁–C₄-haloalkylthio, C₁–C₆-alkylamino, C₁–C₆-dialkylamino, C₁–C₄-alkylcarbonyl, C₃–C₆-cycloalkylcarbonyl, C₁–C₄-alkylcarbonyloxy, C₃–C₆-cycloalkylcarbonyloxy, benzoyl, benzoyloxy, phenyl, phenoxy or phenylthio, where the phenyl radicals in turn may carry from one to five halogen atoms and/or from one to three of the following groups: cyano, nitro, C₁–C₄-alkyl, C₁–C₄-haloalkyl, C₁–C₄-alkoxy, C₁–C₄-haloalkoxy, C₁–C₄-alkylthio or C₁–C₄-haloalkylthio, and R¹ is not benzyl or substituted benzyl;

C₁–C₆-alkylcarbonyl or C₃–C₆-cycloalkylcarbonyl as stated above in general and in particular, where these groups may carry from one to five halogen atoms as stated above in general and in particular and/or one or two of the following radicals stated above in general and in particular: C₃–C₆-cycloalkyl, C₁–C₄-alkoxy, C₁–C₄-haloalkoxy, C₁–C₄-alkylthio, C₁–C₄-haloalkylthio, C₁–C₆-alkylamino, C₁–C₆-dialkylamino, phenyl, phenoxy or phenylthio, where the phenyl radicals in turn may carry from one to five halogen atoms and/or from one to three of the following groups: cyano, nitro, C₁–C₄-alkyl, C₁–C₄-haloalkyl, C₁–C₄-alkoxy, C₁–C₄-haloalkoxy, C₁–C₄-alkylthio or C₁–C₄-haloalkylthio;

C₃–C₆-alkenyl or C₃–C₆-alkynyl as stated above in general and in particular, where these groups may carry from one to five halogen atoms as stated above in general and in particular and/or one or two of the following radicals stated above in general and in particular: C₃–C₆-cycloalkyl, C₁–C₄-alkoxy, C₁–C₄-haloalkoxy, C₁–C₄-alkylthio, C₁–C₄-haloalkylthio, C₁–C₆-alkylamino, C₁–C₆-dialkylamino, C₁–C₄-alkylcarbonyl, C₃–C₆-cycloalkylcarbonyl, C₁–C₄-alkylcarbonyloxy, C₃–C₆-cycloalkylcarbonyloxy, benzoyl, benzoyloxy, phenyl, phenoxy or phenylthio, where the phenyl radicals in turn may carry from one to five halogen atoms and/or from one to three of the following groups: cyano, nitro, C₁–C₄-alkyl, C₁–C₄-haloalkyl, C₁–C₄-alkoxy, C₁–C₄-haloalkoxy, C₁–C₄-alkylthio or C₁–C₄-haloalkylthio;

a 5-membered or 6-membered heterocyclic, aliphatic or aromatic radical containing from one to three hetero atoms selected from the group consisting of oxygen, sulfur and nitrogen, as stated above in general and in particular, where this radical may carry one or two of the following substituents stated above in general and in particular: halogen, C₁–C₄-alkyl, C₃–C₆-cycloalkyl, C₁–C₄-alkoxy or phenyl, where the phenyl radicals in turn may carry from one to five halogen atoms as stated above in general and in particular and/or from one to three of the following groups stated above in general and in particular: cyano, nitro, C₁–C₄-alkyl, C₁–C₄-haloalkyl, C₁–C₄-alkoxy, C₁–C₄-haloalkoxy, C₁–C₄-alkylthio or C₁–C₄-haloalkylthio, or —C(=O)—R, where R is phenyl or one of the 5-membered or 6-membered heterocyclic, aliphatic or aromatic radicals which are stated above in general and in particular and contain from one to three hetero atoms selected from the group consisting of oxygen, sulfur and nitrogen, where these radicals may carry one or two of the following substituents stated above in general and in particular: cyano, nitro, halogen, C₁–C₄-alkyl, C₁–C₄-haloalkyl, C₁–C₄-alkoxy, C₁–C₄-haloalkoxy, C₁–C₄-alkylthio, C₁–C₄-haloalkylthio or phenyl, and R² is hydrogen or C₁–C₄-alkyl as stated above in general and in particular.

Examples of particularly preferred compounds of the general formula I

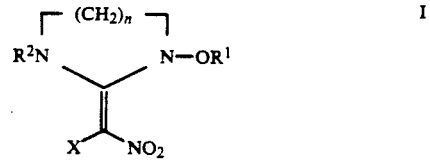

are summarized in the Table below.

TABLE

| R¹ | X | n | R² |
|---|---|---|---|
| —CH₂—CH₂—CH₃ | H | 1 | H |
| —CH(CH₃)₂ | H | 1 | H |
| —CH(CH₃)₂ | H | 1 | CH₃ |
| —CH₂—(CH₂)₃—CH₃ | H | 1 | H |
| —CH(C₂H₅)(CH₃) | H | 1 | H |
| —CH₂CH—(CH₃)₂ | H | 1 | H |
| —C(CH₃)₃ | H | 1 | H |
| —CH₂—CH=CH₂ | H | 1 | H |
| —CH₂—CH=CH₂ | H | 1 | CH₃ |
| —CH₂—CH=CH₂ | H | 1 | C₂H₅ |
| —CH₂—CH=CH—CH₃ | H | 1 | H |
| —CH₂—CH=CH—(CH₂)₂—CH₃ | H | 1 | H |
| —CH₂—CH₂=C(=CH₂)(CH₃) | H | 1 | H |
| —CH(CH₃)—CH=CH₂ | H | 1 | H |
| —CH₂—CH₂—CH=CH₂ | H | 1 | H |
| —CH₂—C≡CH | H | 1 | H |
| —CH₂—C≡CH₃ | H | 1 | H |
| —CH₂—C≡C—CH₃ | H | 1 | CH₃ |
| —CH(CH₃)—C≡CH | H | 1 | H |
| —CH₂—CBr₃ | H | 1 | H |
| —CH₂—CCl₃ | H | 1 | H |
| —CH₂—CH₂—Br | H | 1 | H |
| —CH₂—CF₂—Br | H | 1 | H |
| —CH₂—CF₂—Cl | H | 1 | H |
| —CH₂—CF₃ | H | 1 | H |
| —CH₂—CF₃ | H | 1 | CH₃ |
| —CH₂—CH₂—CH(Cl)—CH₂Cl | H | 1 | H |

TABLE-continued

| R¹ | X | n | R² |
|---|---|---|---|
| —CH(CH₂Cl)CH=CH₂ | H | 1 | H |
| —CH₂—CH=CH₂—CH₂Cl | H | 1 | H |
| —CH₂—C(Cl)=CH₂ | H | 1 | H |
| —CH₂—C(Cl)=CH₂ | H | 1 | CH₃ |
| —CH₂—C(CH₃)(CH₂Cl)₂ | H | 1 | H |
| —CH₂—CH₂Cl | H | 1 | H |
| —CH₂C(CH₃)₂(CH₂Cl) | H | 1 | H |
| —CH₂—CH₂CF=CF₂ | H | 1 | H |
| —CH₂—Cyclopropyl | H | 1 | H |
| —CH₂—Cyclopropyl | H | 1 | CH₃ |
| —CH₂—Cyclopentyl | H | 1 | H |
| —CH₂—Cyclohexyl | H | 1 | H |
| —CH₂—O—CH₂—CH₃ | H | 1 | H |
| —CH₂—O—CH₃ | H | 1 | H |
| —CH₂—CH₂—O—CH₃ | H | 1 | H |
| —CH₂—CH₂—O—C₂H₅ | H | 1 | H |
| —CH₂—CH₂—O—C₂H₅ | H | 1 | CH₃ |
| —C(CH₃)₂—O—CH₃ | H | 1 | H |
| —CH₂CH₂—O—CH₂—CH₂Cl | H | 1 | H |
| —CH₂—CH₂—O—CH₂—CF₃ | H | 1 | H |
| —CH₂—(CH₂)₂—O—CH₃ | H | 1 | H |
| —CH₂—CH₂—CH=CH—CH₂—O—CH₃ | H | 1 | H |
| —CH₂—CH₂—N(CH₃)₂ | H | 1 | H |
| —CH₂—CH₂—CH₂—N(C₂H₅)₂ | H | 1 | H |
| —CH₂—CH₂—S—CH₃ | H | 1 | H |
| —CH₂—CH₂—S—C(CH₃)₃ | H | 1 | H |
| —CH₂—CH₂—S—CHF₂ | H | 1 | H |
| —CH₂-Phenyl | H | 1 | H |
| —CH₂-Phenyl | H | 1 | CH₃ |
| —CH₂-Phenyl | H | 1 | C₂H₅ |
| —CH₂-Phenyl | H | 1 | CH(CH₃)₂ |
| —CH₂—[4-Cl-Phenyl] | H | 1 | H |
| —CH₂—[3-Cl-Phenyl] | H | 1 | H |
| —CH₂—[2,4-Cl₂-Phenyl] | H | 1 | H |
| —CH₂—[3-CF₃-Phenyl] | H | 1 | H |
| —CH₂—[4-(OCF₃)-Phenyl] | H | 1 | H |
| —CH₂—[2-(OCH₃)-Phenyl] | H | 1 | H |
| —CH₂—[2,4,6-(CH₃)₃-Phenyl] | H | 1 | H |
| —CH₂—[4=(SCH₃)-Phenyl] | H | 1 | H |
| —CH₂—CH=CH—CH₂—[4-F-Phenyl] | H | 1 | H |
| —CH₂—CH=CH—CH₂—[4-(C(CH₃)₃)-Phenyl] | H | 1 | H |
| —CH₂—(CH₂)₂-Phenyl] | H | 1 | H |
| —CH₂—CH₂-Phenyl] | H | 1 | H |
| —CH₂—C≡C—CH₂-Phenyl] | H | 1 | H |
| —CH₂—(CH₂)₂—O-Phenyl | H | 1 | H |
| —CH₂—CH(OCH₂CH₃)₂ | H | 1 | H |
| —CH₂—CH(OCH₃)₂ | H | 1 | H |
| —CH₂—C(OCH₃)₂CH₃ | H | 1 | H |
| —CH₂—CH=CH-Phenyl | H | 1 | H |
| —CH₂—CH₂—O-Phenyl | H | 1 | H |
| —CH₂—[tetrahydrofuran-2-yl] | H | 1 | H |
| —CH₂—CH₂—[4-NO₂-Phenyl] | H | 1 | H |
| —CH₂—(CH₂)₈—CH₃ | H | 1 | H |
| —CH₂—(CH₂)₂-Phenyl | H | 1 | H |
| —CH₂—C(Br)=CH₂ | H | 1 | H |
| —CH₂—C(CH₃)₃ | H | 1 | H |
| —CH₂—CH(CH₃)-Phenyl | H | 1 | H |
| —CH₂—CH₂—O—[4-F-Phenyl] | H | 1 | H |
| —CH₂—(CH₂)₃—O-Phenyl | H | 1 | H |
| —CH₂—CH=C(CH₃)₂ | H | 1 | H |
| —CH₂—CH₂—[1,3-dioxan-2-yl] | H | 1 | H |
| —CH₂—CH₂—O—[2-Cl-Phenyl] | H | 1 | H |
| —CH₂—CH₂—O—[4-Cl-Phenyl] | H | 1 | H |
| —CH₂—CH₂—O—[2,6-Cl₂-Phenyl] | H | 1 | H |
| —CH₂—CH₂—O—[2-CH₃, 4-Cl-Phenyl] | H | 1 | H |
| —CH₂—CH₂—O—[4-Br-Phenyl] | H | 1 | H |
| —CH₂—CH₂—O—[3-F-Phenyl] | H | 1 | H |
| —CH₂—CH₂—O—[3-CH₃-Phenyl] | H | 1 | H |
| —CH₂—CH₂—O—[4-CH₃-Phenyl] | H | 1 | H |

TABLE-continued
| R¹ | X | n | R² |
|---|---|---|---|
| —CH₂—CH₂—O—[2,4,6-Cl₃-Phenyl] | H | 1 | H |
| —CH₂—CH₂—[4-F-Phenyl] | H | 1 | H |
| —CH₂—CH(CH₃)—CH₂—[4-F-Phenyl] | H | 1 | H |
| —CH₂—CH₂C(CH₃)₂—[4-Cl-Phenyl] | H | 1 | H |
| —CH₂—CH₂—CH(CH₃)₂ | H | 1 | H |
| —CH₂—(CH₂)₃—O—[2-F-Phenyl] | H | 1 | H |
| 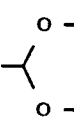 | H | 1 | H |
| 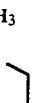 | H | 1 | H |
| —CH₂—CH₂—N(C₂H₅)₂ | H | 1 | H |
|  | H | 1 | H |
| —CH₂—CH=CCl₂ | H | 1 | H |
| —CH₂—C(O)OCH₃ | H | 1 | H |
| 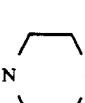 | H | 1 | H |
| —CH₂—C(O)OCH₂-Phenyl | H | 1 | H |
| —CH₂—C(O)OCH₂—CH₃ | H | 1 | H |
| —CH₂C(O)-Phenyl | H | 1 | H |
| —CH₂—C(O)—CH₂—CH₃ | H | 1 | H |
| —CH₂—CH₂—CH₂—O—C(O)CH₃ | H | 1 | H |
| —CH₂—CH₂—CH₂—O—C(O)Phenyl | H | 1 | H |
| —C(O)—CH₃ | H | 1 | H |
|  | H | 1 | H |
| 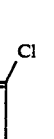 | H | 1 | H |
|  | H | 1 | H |
| —C(O)-Phenyl | H | 1 | H |
| 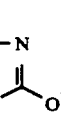 | H | 1 | H |
| 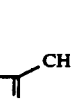 | H | 1 | H |

TABLE-continued
| R¹ | X | n | R² |
|---|---|---|---|
| 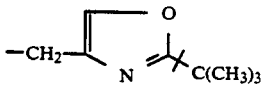 | H | 1 | H |
| 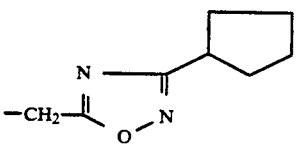 | H | 1 | H |
| 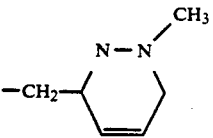 | H | 1 | H |
| 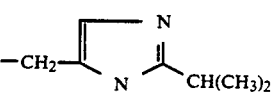 | H | 1 | H |
| 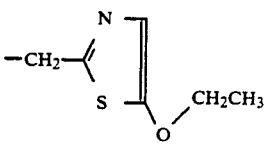 | H | 1 | H |
| 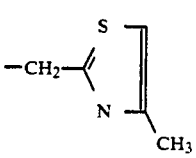 | H | 1 | H |
| 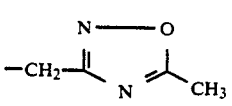 | H | 1 | H |
| 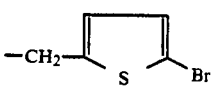 | H | 1 | H |
| 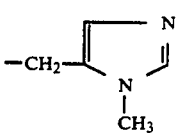 | H | 1 | H |
| 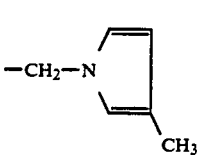 | H | 1 | H |
| 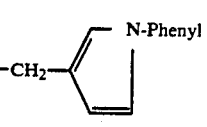 | H | 1 | H |
| 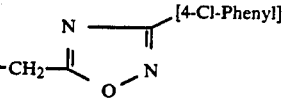 | H | 1 | H |

TABLE-continued
| R¹ | X | n | R² |
|---|---|---|---|
| 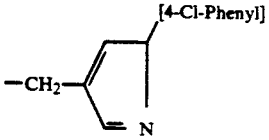 | H | 1 | H |
| 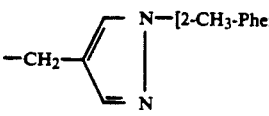 | H | 1 | H |
| 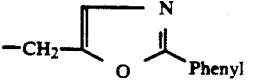 | H | 1 | H |
| 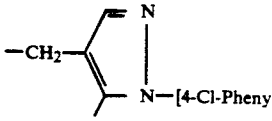 | H | 1 | H |
| 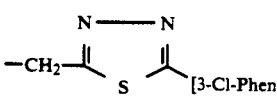 | H | 1 | H |
| 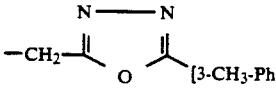 | H | 1 | H |
| —CH₂—CH₂—S-Phenyl | H | 1 | H |
| 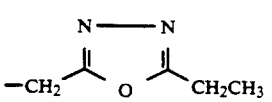 | H | 1 | H |
| 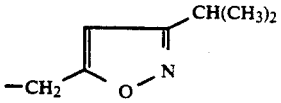 | H | 1 | H |
| 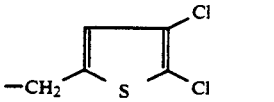 | H | 1 | H |
| 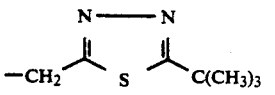 | H | 1 | H |
| 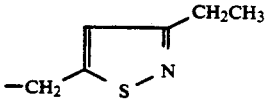 | H | 1 | H |
| 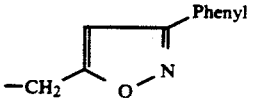 | H | 1 | H |
| 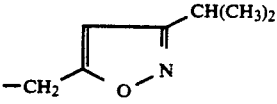 | H | 1 | H |

TABLE-continued
| R¹ | X | n | R² |
|---|---|---|---|
| 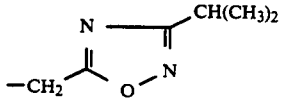 | H | 1 | H |
| 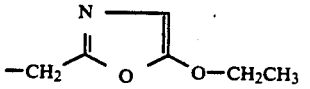 | H | 1 | H |
| 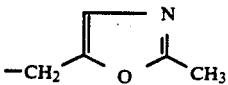 | H | 1 | H |
| 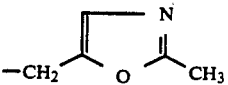 | H | 1 | H |
| 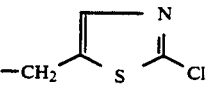 | H | 1 | H |
| 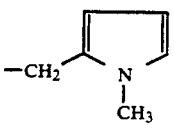 | H | 1 | H |
| 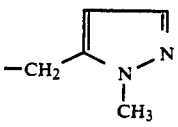 | H | 1 | H |
| 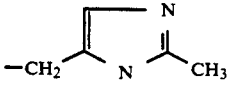 | H | 1 | H |
| 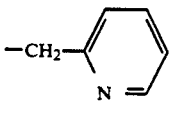 | H | 1 | H |
| 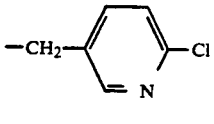 | H | 1 | H |
| 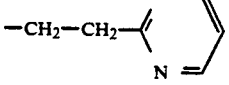 | H | 1 | H |
| 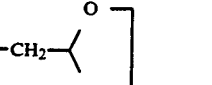 | H | 1 | H |
| 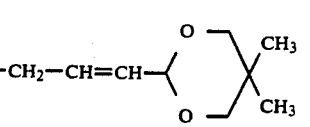 | H | 1 | H |

TABLE-continued

| R¹ | X | n | R² |
|---|---|---|---|
| -CH₂-(pyrimidin-5-yl) | H | 1 | H |
| -CH₂-(2-methylpyrimidin-5-yl) | H | 1 | H |
| -CH₂-(1,2,5-thiadiazol-3-yl) | H | 1 | H |
| -CH₂-(1-ethylpyrazol-4-yl) | H | 1 | H |
| -CH₂-(3-trifluoromethylfuran-4-yl) | H | 1 | H |
| -CH₂-(2-chloropyrimidin-5-yl) | H | 1 | H |
| -CH₂-(6-trifluoromethylpyridazin-3-yl) | H | 1 | H |
| -CH₂-(6-chloropyridin-2-yl) | H | 1 | H |
| -CH₂-(1,3-dioxolan-2-yl) | H | 0 | CH₃ |
| -CH₂-(1,3-dioxolan-2-yl) | H | 0 | C₂H₅ |
| -CH₂-(1,3-dioxolan-2-yl) | H | 0 | CH(CH₃)₂ |
| -CH₂-(1,3-dioxolan-2-yl) | -CH₃ | 0 | H |

TABLE-continued

| R¹ | X | n | R² |
|---|---|---|---|
| -CH₂-(1,3-dioxolan-2-yl) | -CF₃ | 0 | H |
| -CH₂-(1,3-dioxolan-2-yl) | -Cl | 0 | H |
| -CH₂-(1,3-dioxolan-2-yl) | -COCH₃ | 0 | H |
| -CH₂-(1,3-dioxolan-2-yl) | -COCCl₃ | 0 | H |
| -CH₂-(1,3-dioxolan-2-yl) | -CH(OH)CCl₃ | 0 | H |
| -CH₂-(1,3-dioxolan-2-yl) | -COOC₂H₅ | 0 | H |
| -CH₂-(1,3-dioxolan-2-yl) | -COO-Phenyl | 0 | H |
| -CH₂-(1,3-dioxolan-2-yl) | -S-Phenyl | 0 | H |
| -CH₂-(1,3-dioxolan-2-yl) | -CH₂-S-Phenyl | 0 | H |
| -CH₂-(1,3-dioxolan-2-yl) | -CO-Phenyl | 0 | H |
| -CH₂-(1,3-dioxolan-2-yl) | -Phenyl | 0 | H |
| -CH₂-(1,3-dioxolan-2-yl) | -S-(CH₂)₃CH₃ | 0 | H |
| CH₃ | H | 0 | CH₃ |
| CH₃ | H | 0 | C₂H₅ |
| CH₃ | H | 0 | CH₂(CH₂)₂CH₃ |
| CH₃ | COCH₃ | 0 | H |
| CH₃ | CH₃ | 0 | H |
| CH₃ | CF₃ | 0 | H |

TABLE-continued

| R$^1$ | X | n | R$^2$ |
|---|---|---|---|
| CH$_3$ | Cl | 0 | H |
| CH$_3$ | CHF$_2$ | 0 | H |
| CH$_3$ | CH(OH)CCl$_3$ | 0 | H |
| CH$_3$ | Br | 0 | H |
| CH$_3$ | —CH$_2$S-Phenyl | 0 | H |
| CH$_3$ | —S-Phenyl | 0 | H |
| CH$_3$ | —S—[4-Cl-Phenyl] | 0 | H |
| CH$_3$ | -Phenyl | 0 | H |
| CH$_3$ | —COOC$_2$H$_5$ | 0 | H |
| CH$_3$ | —COOCH$_3$ | 0 | H |
| CH$_3$ | —COO-Phenyl | 0 | H |
| CH$_3$ | —CO-Phenyl | 0 | H |
| CH$_3$ | —COOCCl$_3$ | 0 | H |
| —CH$_2$CH$_3$ | H | 0 | H |
| —CH$_2$CH$_3$ | H | 0 | CH$_3$ |
| —CH$_2$CH$_3$ | CH$_2$OCH$_3$ | 0 | H |
| —C(CH$_3$)$_3$ | H | 0 | H |
| —CH(CH$_3$)$_2$ | CH$_3$ | 0 | H |
| —CH(CH$_3$)$_2$ | Cl | 0 | H |
| —CH(CH$_3$)$_2$ | CH$_2$OH | 0 | H |
| —CH(CH$_3$)$_2$ | CH(OH)CCl$_3$ | 0 | H |
| —CH(CH$_3$)$_2$ | CF$_3$ | 0 | H |
| —CH(CH$_3$)$_2$ | H | 0 | CH$_3$ |
| —CH$_2$C=CH$_2$ | H | 0 | CH$_3$ |
| —CH$_2$C≡CH | —COO-Phenyl | 0 | H |
| —CH$_2$C≡CH | —CH(OH)CCl$_3$ | 0 | H |
| —CH$_2$C≡CH | —CH$_3$ | 0 | H |
| —CH$_2$CF$_3$ | H | 0 | CH$_3$ |
| —CH$_2$CF$_3$ | H | 0 | C$_2$H$_5$ |
| —CH$_2$CF$_3$ | H | 0 | CH(CH$_3$)$_2$ |
| —CH$_2$CF$_3$ | —CH(OH)CCl$_3$ | 0 | H |
| —CH$_2$CF$_3$ | Cl | 0 | H |
| —CH$_2$CF$_3$ | CF$_3$ | 0 | H |
| —CH$_2$CF$_3$ | CH(OH)CCl$_3$ | 0 | H |
| —CH$_2$CH$_2$CF=CF$_2$ | H | 0 | H |
| —CH$_2$CH$_2$CF=CF$_2$ | H | 0 | CH$_3$ |
| —CH$_2$CH$_2$CF=CF$_2$ | Cl | 0 | H |
| —CH$_2$CH$_2$CF=CF$_2$ | CH(OH)CCl$_3$ | 0 | H |
| —CH$_2$CH$_2$CF=CF$_2$ | S-Phenyl | 0 | H |
| —CH$_2$CH$_2$CF=CF$_2$ | —COOCH$_3$ | 0 | H |
| —CH$_2$-Cyclopropyl | H | 0 | H |
| —CH$_2$-Cyclopropyl | H | 0 | CH$_3$ |
| —CH$_2$-Cyclopropyl | H | 0 | CH(CH$_3$)$_2$ |
| —CH$_2$-Cyclopropyl | CF$_3$ | 0 | H |
| —CH$_2$-Cyclopropyl | Cl | 0 | H |
| —CH$_2$-Cyclopropyl | CH(OH)CCl$_3$ | 0 | H |
| —CH$_2$-Cyclopropyl | —COO-Phenyl | 0 | H |
| —CH$_2$-Cyclopropyl | —CO-Phenyl | 0 | H |
| —CH$_2$-Cyclopropyl | —COOC$_2$H$_5$ | 0 | H |
| —CH$_2$-Cyclopropyl | H | 0 | H |
| —CH$_2$-Cyclopropyl | H | 0 | CH$_3$ |
| —CH$_2$-Cyclopropyl | H | 0 | C$_2$H$_5$ |
| —CH$_2$-Cyclopropyl | —S-Phenyl | 0 | H |
| —CH$_2$-Cyclopropyl | —S—(CH$_2$)$_3$CH$_3$ | 0 | H |
| —CH$_2$-Cyclopropyl | —COCH$_3$ | 0 | H |
| —CH$_2$-Cyclopropyl | —COCCl$_3$ | 0 | H |
| —CH$_2$-Cyclopropyl | —CH$_2$—S-Phenyl | 0 | H |
| —CH$_2$-Cyclopropyl | —CH$_3$ | 0 | H |
| —CH$_2$CH$_2$OCH$_3$ | H | 0 | H |
| —CH$_2$CH$_2$OCH$_3$ | H | 0 | CH$_3$ |
| —CH$_2$CH$_2$OCH$_3$ | H | 0 | C$_2$H$_5$ |
| —CH$_2$CH$_2$OCH$_3$ | H | 0 | CH(CH$_3$)$_2$ |
| —CH$_2$CH$_2$OCH$_3$ | Cl | 0 | H |
| —CH$_2$CH$_2$OCH$_3$ | CH$_3$ | 0 | H |
| —CH$_2$CH$_2$OCH$_3$ | COCH$_3$ | 0 | H |
| —CH$_2$CH$_2$OCH$_3$ | C(OH)CCl$_3$ | 0 | H |
| —CH$_2$CH$_2$OCH$_3$ | COCF$_3$ | 0 | H |
| —CH$_2$CH$_2$OCH$_3$ | —S-Phenyl | 0 | H |
| —CH$_2$CH$_2$OCH$_3$ | —CH$_2$—S-Phenyl | 0 | H |
| —CH$_2$CH$_2$OCH$_3$ | —CHF$_2$ | 0 | H |
| —CH$_2$CH$_2$OCH$_3$ | —COOCH$_3$ | 0 | H |
| —CH$_2$CH$_2$OCH$_3$ | —COO-Phenyl | 0 | H |
| —CH$_2$CH$_2$CH$_2$N(C$_2$H$_5$)$_2$ | —CH$_3$ | 0 | H |
| —CH$_2$CH$_2$CH$_2$N(C$_2$H$_5$)$_2$ | —CHF$_2$ | 0 | H |
| —CH$_2$CH$_2$CH$_2$N(C$_2$H$_5$)$_2$ | H | 0 | —CH$_3$ |
| —CH$_2$CH$_2$CH$_2$N(C$_2$H$_5$)$_2$ | H | 0 | —C$_2$H$_5$ |
| —CH$_2$CH$_2$CH$_2$N(C$_2$H$_5$)$_2$ | H | 0 | —CH$_2$—(CH$_2$)$_2$—CH$_3$ |
| —CH$_2$CH$_2$CH$_2$N(C$_2$H$_5$)$_2$ | —Cl | 0 | H |
| —CH$_2$—CH$_2$—CH$_2$—N(C$_2$H$_5$)$_2$ | —COCH$_3$ | 0 | H |
| —CH$_2$—CH$_2$—CH$_2$—N(C$_2$H$_5$)$_2$ | —COCF$_3$ | 0 | H |
| —CH$_2$—CH$_2$—CH$_2$—N(C$_2$H$_5$)$_2$ | —C(OH)CCl$_3$ | 0 | H |

TABLE-continued

| R¹ | X | n | R² |
|---|---|---|---|
| —CH₂—CH₂—CH₂—N(C₂H₅)₂ | —COOC₂H₅ | 0 | H |
| —CH₂—CH₂—CH₂—N(C₂H₅)₂ | —COO-Phenyl | 0 | H |
| —CH₂—CH₂—CH₂—N(C₂H₅)₂ | —CH₂S-Phenyl | 0 | H |
| —CH₂—CH₂—OCH₂—CF₃ | H | 0 | H |
| —CH₂—CH₂—OCH₂—CF₃ | H | 0 | —CH₃ |
| —CH₂—CH₂—OCH₂—CF₃ | H | 0 | —C₂H₅ |
| —CH₂—CH₂—OCH₂—CF₃ | H | 0 | —CH(CH₃)₂ |
| —CH₂—CH₂—OCH₂—CF₃ | —Br | 0 | H |
| —CH₂—CH₂—OCH₂—CF₃ | —CF₃ | 0 | H |
| —CH₂—CH₂—OCH₂—CF₃ | —CH₃ | 0 | H |
| —CH₂—CH₂—OCH₂—CF₃ | —COCH₃ | 0 | H |
| —CH₂—CH₂—OCH₂—CF₃ | —COCCl₃ | 0 | H |
| —CH₂—CH₂—OCH₂—CF₃ | —COOC₂H₅ | 0 | H |
| —CH₂—CH₂—OCH₂—CF₃ | —COO-Phenyl | 0 | H |
| —CH₂—CH₂—OCH₂—CF₃ | —CH₂S-Phenyl | 0 | H |
| —CH₂—CH₂—OCH₂—CF₃ | —S-Phenyl | 0 | H |
| —CH₂—CH₂—S—CH₃ | H | 0 | CH₃ |
| —CH₂—CH₂—S—CH₃ | H | 0 | C₂H₅ |
| —CH₂—CH₂—S—CH₃ | H | 0 | —CH(CH₃)₂ |
| —CH₂—CH₂—S—CH₃ | —Cl | 0 | H |
| —CH₂—CH₂—S—CH₃ | —CHF₂ | 0 | H |
| —CH₂—CH₂—S—CH₃ | —CH(OH)CCl₃ | 0 | H |
| —CH₂—CH₂—S—CH₃ | —CH₃ | 0 | H |
| —CH₂—CH₂—S—CH₃ | —COCH₃ | 0 | H |
| —CH₂—CH₂—S—CH₃ | —COCF₃ | 0 | H |
| —CH₂—CH₂—S—CH₃ | —COOCH₃ | 0 | H |
| —CH₂—CH₂—S—CH₃ | —COO-Phenyl | 0 | H |
| —CH₂—CH₂—S—CH₃ | —CO-Phenyl | 0 | H |
| —CH₂—CH₂—S—CH₃ | —S-Phenyl | 0 | H |
| —CH₂—CH₂—S—CH₃ | —CH₂S-Phenyl | 0 | H |
| —CH₂—CH₂—SCHF₂ | H | 0 | CH₃ |
| —CH₂—CH₂—SCHF₂ | H | 0 | C₂H₅ |
| —CH₂—CH₂—SCHF₂ | H | 0 | CH(CH₃)₂ |
| —CH₂—CH₂—SCHF₂ | —CH₃ | 0 | H |
| —CH₂—CH₂—SCHF₂ | —CF₃ | 0 | H |
| —CH₂—CH₂—SCHF₂ | —Cl | 0 | H |
| —CH₂—CH₂—SCHF₂ | —COCH₃ | 0 | H |
| —CH₂—CH₂—SCHF₂ | —COCCl₃ | 0 | H |
| —CH₂—CH₂—SCHF₂ | —CH(OH)CCl₃ | 0 | H |
| —CH₂—CH₂—SCHF₂ | —COOC₂H₅ | 0 | H |
| —CH₂—CH₂—SCHF₂ | —COO-Phenyl | 0 | H |
| —CH₂—CH₂—SCHF₂ | —S-Phenyl | 0 | H |
| —CH₂—CH₂—SCHF₂ | —CH₂S-Phenyl | 0 | H |
| —CH₂—CH₂—SCHF₂ | —CO-Phenyl | 0 | H |
| —CH₂—CH₂—SCHF₂ | -Phenyl | 0 | H |
| —CH₂—CH₂—SCHF₂ | —S—(CH₂)₃CH₃ | 0 | H |
| —CH₂-Phenyl | H | 0 | CH₃ |
| —CH₂-Phenyl | H | 0 | C₂H₅ |
| —CH₂-Phenyl | H | 0 | CH(CH₃)₂ |
| —CH₂-Phenyl | —CH₃ | 0 | H |
| —CH₂-Phenyl | —CF₃ | 0 | H |
| —CH₂-Phenyl | —Cl | 0 | H |
| —CH₂-Phenyl | —COCH₃ | 0 | H |
| —CH₂-Phenyl | —COCCl₃ | 0 | H |
| —CH₂-Phenyl | —CH(OH)CCl₃ | 0 | H |
| —CH₂-Phenyl | —COOC₂H₅ | 0 | H |
| —CH₂-Phenyl | —COO-Phenyl | 0 | H |
| —CH₂-Phenyl | —S-Phenyl | 0 | H |
| —CH₂-Phenyl | —CH₂—S-Phenyl | 0 | H |
| —CH₂-Phenyl | —CO-Phenyl | 0 | H |
| —CH₂-Phenyl | -Phenyl | 0 | H |
| —CH₂-Phenyl | —S—(CH₂)₃CH₃ | 0 | H |
| —CH₂—[2,4-Cl₂-Phenyl] | H | 0 | CH₃ |
| —CH₂—[2,4-Cl₂-Phenyl] | H | 0 | C₂H₅ |
| —CH₂—[2,4-Cl₂-Phenyl] | H | 0 | CH(CH₃)₂ |
| —CH₂—[2,4-Cl₂-Phenyl] | —CH₃ | 0 | H |
| —CH₂—[2,4-Cl₂-Phenyl] | —CF₃ | 0 | H |
| —CH₂—[2,4-Cl₂-Phenyl] | —Cl | 0 | H |
| —CH₂—[2,4-Cl₂-Phenyl] | —COCH₃ | 0 | H |
| —CH₂—[2,4-Cl₂-Phenyl] | —COCCl₃ | 0 | H |
| —CH₂—[2,4-Cl₂-Phenyl] | —CH(OH)CCl₃ | 0 | H |
| —CH₂—[2,4-Cl₂-Phenyl] | —COOC₂H₅ | 0 | H |
| —CH₂—[2,4-Cl₂-Phenyl] | —COO-Phenyl | 0 | H |
| —CH₂—[2,4-Cl₂-Phenyl] | —S-Phenyl | 0 | H |
| —CH₂—[2,4-Cl₂-Phenyl] | —CH₂—S-Phenyl | 0 | H |
| —CH₂—[2,4-Cl₂-Phenyl] | —CO-Phenyl | 0 | H |
| —CH₂—[2,4-Cl₂-Phenyl] | -Phenyl | 0 | H |
| —CH₂—[2,4-Cl₂-Phenyl] | —S—(CH₂)₃CH₃ | 0 | H |
| —CH₂—CH=CH—CH₂—[4-F-Phenyl] | H | 0 | CH₃ |
| —CH₂—CH=CH—CH₂—[4-F-Phenyl] | H | 0 | C₂H₅ |
| —CH₂—CH=CH—CH₂—[4-F-Phenyl] | H | 0 | CH(CH₃)₂ |

TABLE-continued

| R¹ | X | n | R² |
|---|---|---|---|
| —CH₂—CH=CH—CH₂—[4-F-Phenyl] | —CH₃ | 0 | H |
| —CH₂—CH=CH—CH₂—[4-F-Phenyl] | —CF₃ | 0 | H |
| —CH₂—CH=CH—CH₂—[4-F-Phenyl] | —Cl | 0 | H |
| —CH₂—CH=CH—CH₂—[4-F-Phenyl] | —COCH₃ | 0 | H |
| —CH₂—CH=CH—CH₂—[4-F-Phenyl] | —COCCl₃ | 0 | H |
| —CH₂—CH=CH—CH₂—[4-F-Phenyl] | —CH(OH)CCl₃ | 0 | H |
| —CH₂—CH=CH—CH₂—[4-F-Phenyl] | —COOC₂H₅ | 0 | H |
| —CH₂—CH=CH—CH₂—[4-F-Phenyl] | —COO-Phenyl | 0 | H |
| —CH₂—CH=CH—CH₂—[4-F-Phenyl] | —S-Phenyl | 0 | H |
| —CH₂—CH=CH—CH₂—[4-F-Phenyl] | —CH₂—S-Phenyl | 0 | H |
| —CH₂—CH=CH—CH₂—[4-F-Phenyl] | —CO-Phenyl | 0 | H |
| —CH₂—CH=CH—CH₂—[4-F-Phenyl] | -Phenyl | 0 | H |
| —CH₂—CH=CH—CH₂—[4-F-Phenyl] | —S—(CH₂)₃CH₃ | 0 | H |
| —CH₂—(CH₂)₂—O-Phenyl | H | 0 | CH₃ |
| —CH₂—(CH₂)₂—O-Phenyl | H | 0 | C₂H₅ |
| —CH₂—(CH₂)₂—O-Phenyl | H | 0 | CH(CH₃)₂ |
| —CH₂—(CH₂)₂—O-Phenyl | —CH₃ | 0 | H |
| —CH₂—(CH₂)₂—O-Phenyl | —CF₃ | 0 | H |
| —CH₂—(CH₂)₂—O-Phenyl | —Cl | 0 | H |
| —CH₂—(CH₂)₂—O-Phenyl | —COCH₃ | 0 | H |
| —CH₂—(CH₂)₂—O-Phenyl | —COCCl₃ | 0 | H |
| —CH₂—(CH₂)₂—O-Phenyl | —CH(OH)CCl₃ | 0 | H |
| —CH₂—(CH₂)₂—O-Phenyl | —COOC₂H₅ | 0 | H |
| —CH₂—(CH₂)₂—O-Phenyl | —COO-Phenyl | 0 | H |
| —CH₂—(CH₂)₂—O-Phenyl | —S-Phenyl | 0 | H |
| —CH₂—(CH₂)₂—O-Phenyl | —CH₂—S-Phenyl | 0 | H |
| —CH₂—(CH₂)₂—O-Phenyl | —CO-Phenyl | 0 | H |
| —CH₂—(CH₂)₂—O-Phenyl | -Phenyl | 0 | H |
| —CH₂—(CH₂)₂—O-Phenyl | —S—(CH₂)₃CH₃ | 0 | H |
| —CH₂-[3-isopropyl-isoxazol-5-yl] | H | 0 | CH₃ |
| —CH₂-[3-isopropyl-isoxazol-5-yl] | H | 0 | C₂H₅ |
| —CH₂-[3-isopropyl-isoxazol-5-yl] | H | 0 | CH(CH₃)₂ |
| —CH₂-[3-isopropyl-isoxazol-5-yl] | —CH₃ | 0 | H |
| —CH₂-[3-isopropyl-isoxazol-5-yl] | —CF₃ | 0 | H |
| —CH₂-[3-isopropyl-isoxazol-5-yl] | —Cl | 0 | H |
| —CH₂-[3-isopropyl-isoxazol-5-yl] | —COCH₃ | 0 | H |
| —CH₂-[3-isopropyl-isoxazol-5-yl] | —COCCl₃ | 0 | H |
| —CH₂-[3-isopropyl-isoxazol-5-yl] | —CH(OH)CCl₃ | 0 | H |

TABLE-continued
| R¹ | X | n | R² |
|---|---|---|---|
| 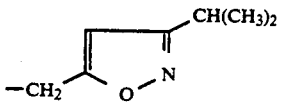 | —COOC$_2$H$_5$ | 0 | H |
| 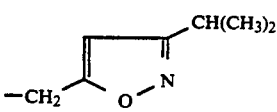 | —COO-Phenyl | 0 | H |
| 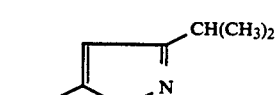 | —S-Phenyl | 0 | H |
| 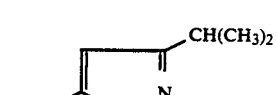 | —CH$_2$—S-Phenyl | 0 | H |
| 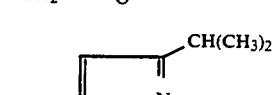 | —CO-Phenyl | 0 | H |
| 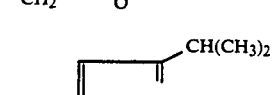 | -Phenyl | 0 | H |
| 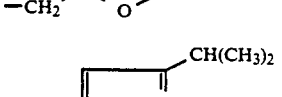 | —S—(CH$_2$)$_3$CH$_3$ | 0 | H |
| 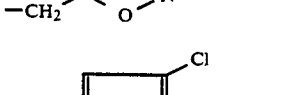 | H | 0 | CH$_3$ |
| 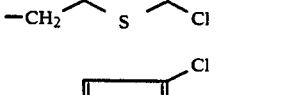 | H | 0 | C$_2$H$_5$ |
| 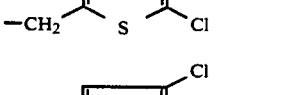 | H | 0 | CH(CH$_3$)$_2$ |
| 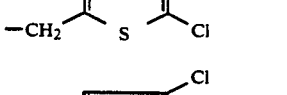 | —CH$_3$ | 0 | H |
| 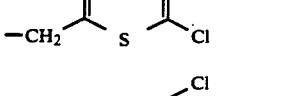 | —CF$_3$ | 0 | H |
| 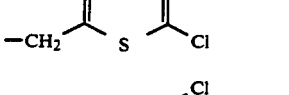 | —Cl | 0 | H |
| 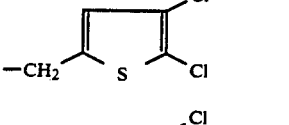 | —COCH$_3$ | 0 | H |

TABLE-continued
| R¹ | X | n | R² |
|---|---|---|---|
| 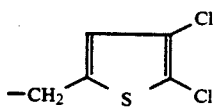 | —COCCl₃ | 0 | H |
| 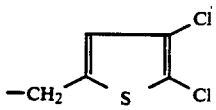 | —CH(OH)CCl₃ | 0 | H |
| 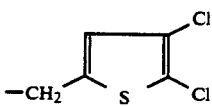 | —COOC₂H₅ | 0 | H |
| 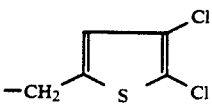 | —COO-Phenyl | 0 | H |
| 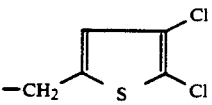 | —S-Phenyl | 0 | H |
| 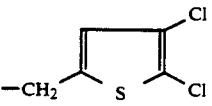 | —CH₂—S-Phenyl | 0 | H |
| 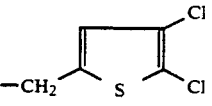 | —CO-Phenyl | 0 | H |
| 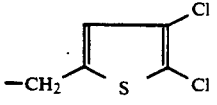 | -Phenyl | 0 | H |
| 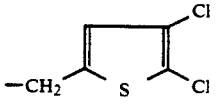 | —S—(CH₂)₃CH₃ | 0 | H |
| 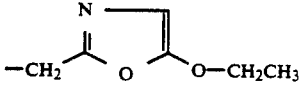 | H | 0 | CH₃ |
| 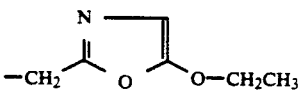 | H | 0 | C₂H₅ |
| 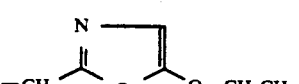 | H | 0 | CH(CH₃)₂ |
|  | —CH₃ | 0 | H |
|  | —CF₃ | 0 | H |

TABLE-continued
| R¹ | X | n | R² |
|---|---|---|---|
| 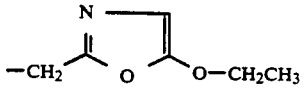 | —Cl | 0 | H |
| 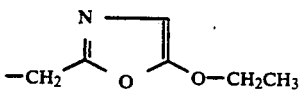 | —COCH$_3$ | 0 | H |
|  | —COCCl$_3$ | 0 | H |
|  | —CH(OH)CCl$_3$ | 0 | H |
|  | —COOC$_2$H$_5$ | 0 | H |
|  | —COO-Phenyl | 0 | H |
| 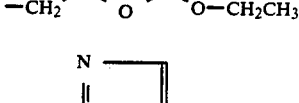 | —S-Phenyl | 0 | H |
| 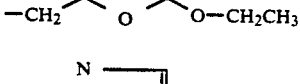 | —CH$_2$—S-Phenyl | 0 | H |
| 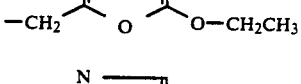 | —CO-Phenyl | 0 | H |
| 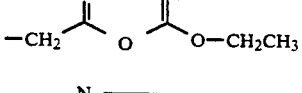 | -Phenyl | 0 | H |
| 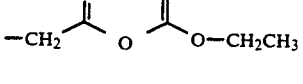 | —S—(CH$_2$)$_3$CH$_3$ | 0 | H |
| 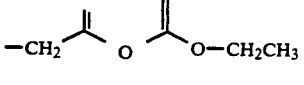 | H | 0 | CH$_3$ |
| 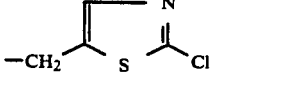 | H | 0 | C$_2$H$_5$ |
| 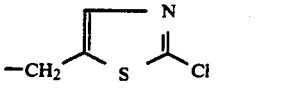 | H | 0 | CH(CH$_3$)$_2$ |
| 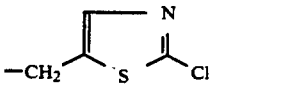 | —CH$_3$ | 0 | H |

TABLE-continued
| R¹ | X | n | R² |
|---|---|---|---|
| 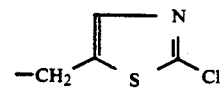 | —CF₃ | 0 | H |
| 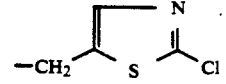 | —Cl | 0 | H |
| 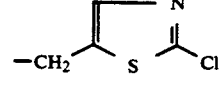 | —COCH₃ | 0 | H |
| 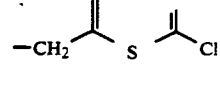 | —COCCl₃ | 0 | H |
| 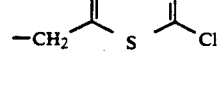 | —CH(OH)CCl₃ | 0 | H |
| 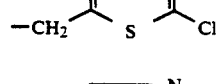 | —COOC₂H₅ | 0 | H |
| 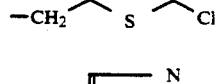 | —COO-Phenyl | 0 | H |
|  | —S-Phenyl | 0 | H |
|  | —CH₂—S-Phenyl | 0 | H |
|  | —CO-Phenyl | 0 | H |
|  | -Phenyl | 0 | H |
| 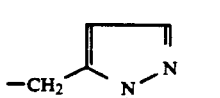 | —S—(CH₂)₃CH₃ | 0 | H |
| 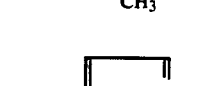 | H | 0 | CH₃ |
| 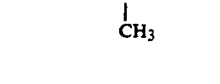 | H | 0 | C₂H₅ |

TABLE-continued

| R¹ | X | n | R² |
|---|---|---|---|
| -CH₂-[pyrazole-N-CH₃] | H | 0 | CH(CH₃)₂ |
| -CH₂-[pyrazole-N-CH₃] | -CH₃ | 0 | H |
| -CH₂-[pyrazole-N-CH₃] | -CF₃ | 0 | H |
| -CH₂-[pyrazole-N-CH₃] | -Cl | 0 | H |
| -CH₂-[pyrazole-N-CH₃] | -COCH₃ | 0 | H |
| -CH₂-[pyrazole-N-CH₃] | -COCCl₃ | 0 | H |
| -CH₂-[pyrazole-N-CH₃] | -CH(OH)CCl₃ | 0 | H |
| -CH₂-[pyrazole-N-CH₃] | -COOC₂H₅ | 0 | H |
| -CH₂-[pyrazole-N-CH₃] | -COO-Phenyl | 0 | H |
| -CH₂-[pyrazole-N-CH₃] | -S-Phenyl | 0 | H |
| -CH₂-[pyrazole-N-CH₃] | -CH₂-S-Phenyl | 0 | H |

TABLE-continued
| R¹ | X | n | R² |
|---|---|---|---|
| 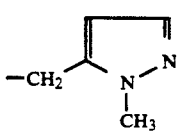 | —CO-Phenyl | 0 | H |
| 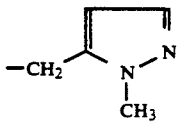 | -Phenyl | 0 | H |
| 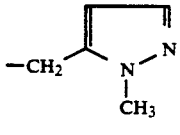 | —S—(CH$_2$)$_3$CH$_3$ | 0 | H |
| 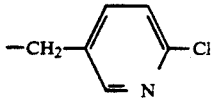 | H | 0 | CH$_3$ |
| 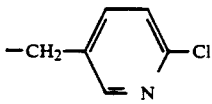 | H | 0 | C$_2$H$_5$ |
| 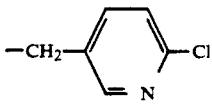 | H | 0 | CH(CH$_3$)$_2$ |
| 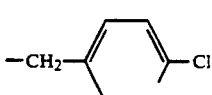 | —CH$_3$ | 0 | H |
| 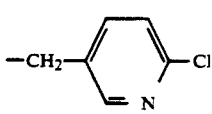 | —CF$_3$ | 0 | H |
| 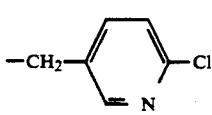 | —Cl | 0 | H |
| 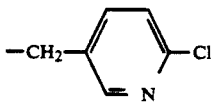 | —COCH$_3$ | 0 | H |
| 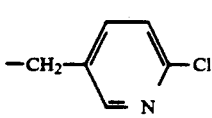 | —COCCl$_3$ | 0 | H |
| 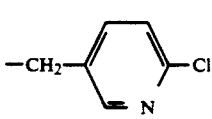 | —CH(OH)CCl$_3$ | 0 | H |

TABLE-continued
| R[1] | X | n | R[2] |
|---|---|---|---|
| 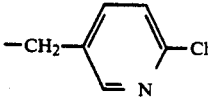 | —COOC$_2$H$_5$ | 0 | H |
| 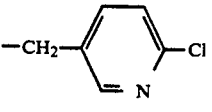 | —COO-Phenyl | 0 | H |
| 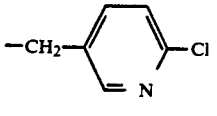 | —S-Phenyl | 0 | H |
| 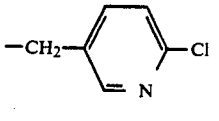 | —CH$_2$—S-Phenyl | 0 | H |
| 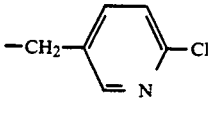 | —CO-Phenyl | 0 | H |
| 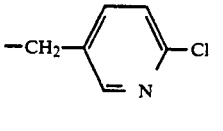 | -Phenyl | 0 | H |
| 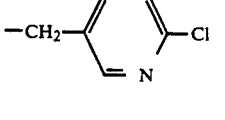 | —S—(CH$_2$)$_3$CH$_3$ | 0 | H |
| 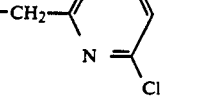 | H | 0 | CH$_3$ |
| 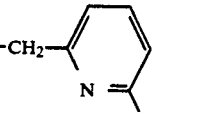 | H | 0 | C$_2$H$_5$ |
| 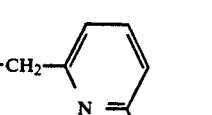 | H | 0 | CH(CH$_3$)$_2$ |
| 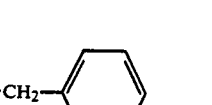 | —CH$_3$ | 0 | H |

TABLE-continued
| R¹ | X | n | R² |
|---|---|---|---|
| 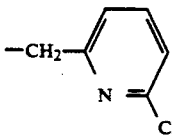—CH₂—(2-chloropyridin-6-yl) | —CF₃ | 0 | H |
| 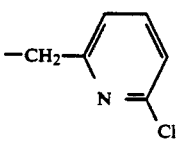—CH₂—(2-chloropyridin-6-yl) | —Cl | 0 | H |
| 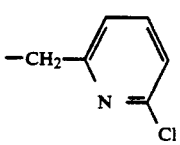—CH₂—(2-chloropyridin-6-yl) | —COCH₃ | 0 | H |
| 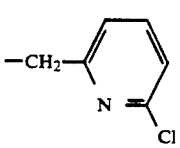—CH₂—(2-chloropyridin-6-yl) | —COCCl₃ | 0 | H |
| 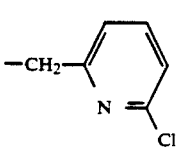—CH₂—(2-chloropyridin-6-yl) | —CH(OH)CCl₃ | 0 | H |
| 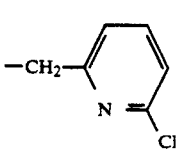—CH₂—(2-chloropyridin-6-yl) | —COOC₂H₅ | 0 | H |
| 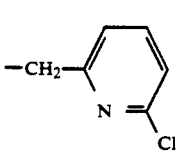—CH₂—(2-chloropyridin-6-yl) | —COO-Phenyl | 0 | H |
| 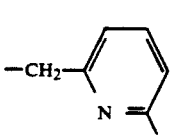—CH₂—(2-chloropyridin-6-yl) | —S-Phenyl | 0 | H |
| 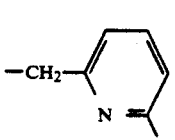—CH₂—(2-chloropyridin-6-yl) | —CH₂—S-Phenyl | 0 | H |
| 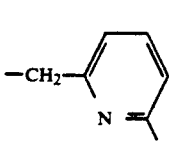—CH₂—(2-chloropyridin-6-yl) | —CO-Phenyl | 0 | H |

TABLE-continued
| R¹ | X | n | R² |
|---|---|---|---|
| 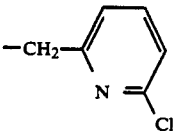 | -Phenyl | 0 | H |
| 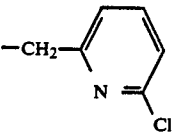 | $-S-(CH_2)_3CH_3$ | 0 | H |
| 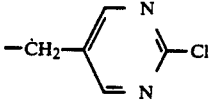 | H | 0 | $CH_3$ |
| 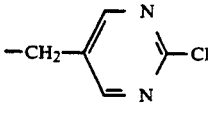 | H | 0 | $C_2H_5$ |
| 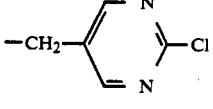 | H | 0 | $CH(CH_3)_2$ |
| 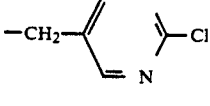 | $-CH_3$ | 0 | H |
| 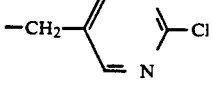 | $-CF_3$ | 0 | H |
| 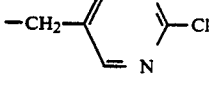 | $-Cl$ | 0 | H |
| 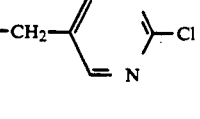 | $-COCH_3$ | 0 | H |
| 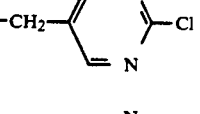 | $-COCCl_3$ | 0 | H |
| 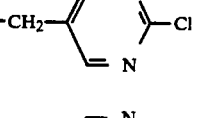 | $-CH(OH)CCl_3$ | 0 | H |
| 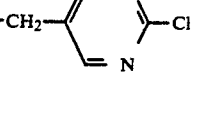 | $-COOC_2H_5$ | 0 | H |

TABLE-continued

| R¹ | X | n | R² |
|---|---|---|---|
| 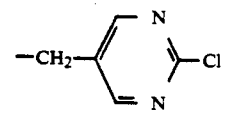 | —COO-Phenyl | 0 | H |
| 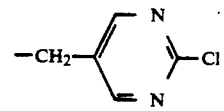 | —S-Phenyl | 0 | H |
| 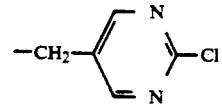 | —CH₂—S-Phenyl | 0 | H |
| 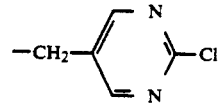 | —CO-Phenyl | 0 | H |
| 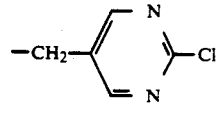 | -Phenyl | 0 | H |
| 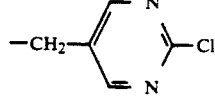 | —S—(CH₂)₃CH₃ | 0 | H |
| —CH₃ | H | 1 | CH₃ |
| —CH₃ | H | 1 | C₂H₅ |
| —CH₃ | H | 1 | CH(CH₃)₂ |
| —CH₃ | —CH₃ | 1 | H |
| —CH₃ | —CF₃ | 1 | H |
| —CH₃ | —Cl | 1 | H |
| —CH₃ | —COCH₃ | 1 | H |
| —CH₃ | —COCCl₃ | 1 | H |
| —CH₃ | —CH(OH)CCl₃ | 1 | H |
| —CH₃ | —COOC₂H₅ | 1 | H |
| —CH₃ | —COO-Phenyl | 1 | H |
| —CH₃ | —S-Phenyl | 1 | H |
| —CH₃ | —CH₂—S-Phenyl | 1 | H |
| —CH₃ | —CO-Phenyl | 1 | H |
| —CH₃ | -Phenyl | 1 | H |
| —CH₃ | —S—(CH₂)₃CH₃ | 1 | H |
| —C₂H₅ | H | 1 | CH₃ |
| —C₂H₅ | H | 1 | C₂H₅ |
| —C₂H₅ | H | 1 | CH(CH₃)₂ |
| —C₂H₅ | —CH₃ | 1 | H |
| —C₂H₅ | —CF₃ | 1 | H |
| —C₂H₅ | —Cl | 1 | H |
| —C₂H₅ | —COCH₃ | 1 | H |
| —C₂H₅ | —COCCl₃ | 1 | H |
| —C₂H₅ | —CH(OH)CCl₃ | 1 | H |
| —C₂H₅ | —COOC₂H₅ | 1 | H |
| —C₂H₅ | —COO-Phenyl | 1 | H |
| —C₂H₅ | —S-Phenyl | 1 | H |
| —C₂H₅ | —CH₂—S-Phenyl | 1 | H |
| —C₂H₅ | —CO-Phenyl | 1 | H |
| —C₂H₅ | -Phenyl | 1 | H |
| —C₂H₅ | —S—(CH₂)₃CH₃ | 1 | H |
| —CH(CH₃)₂ | H | 1 | CH₃ |
| —CH(CH₃)₂ | H | 1 | C₂H₅ |
| —CH(CH₃)₂ | H | 1 | CH(CH₃)₂ |
| —CH(CH₃)₂ | —CH₃ | 1 | H |
| —CH(CH₃)₂ | —CF₃ | 1 | H |
| —CH(CH₃)₂ | —Cl | 1 | H |
| —CH(CH₃)₂ | —COCH₃ | 1 | H |
| —CH(CH₃)₂ | —COCCl₃ | 1 | H |
| —CH(CH₃)₂ | —CH(OH)CCl₃ | 1 | H |
| —CH(CH₃)₂ | —COOC₂H₅ | 1 | H |
| —CH(CH₃)₂ | —COO-Phenyl | 1 | H |

TABLE-continued

| $R^1$ | X | n | $R^2$ |
|---|---|---|---|
| —CH(CH$_3$)$_2$ | —S-Phenyl | 1 | H |
| —CH(CH$_3$)$_2$ | —CH$_2$—S-Phenyl | 1 | H |
| —CH(CH$_3$)$_2$ | —CO-Phenyl | 1 | H |
| —CH(CH$_3$)$_2$ | -Phenyl | 1 | H |
| —CH(CH$_3$)$_2$ | —S—(CH$_2$)$_3$CH$_3$ | 1 | H |
| —CH$_2$—CH—(CH$_3$)$_2$ | H | 1 | CH$_3$ |
| —CH$_2$—CH—(CH$_3$)$_2$ | H | 1 | C$_2$H$_5$ |
| —CH$_2$—CH—(CH$_3$)$_2$ | H | 1 | CH(CH$_3$)$_2$ |
| —CH$_2$—CH—(CH$_3$)$_2$ | —CH$_3$ | 1 | H |
| —CH$_2$—CH—(CH$_3$)$_2$ | —CF$_3$ | 1 | H |
| —CH$_2$—CH—(CH$_3$)$_2$ | —Cl | 1 | H |
| —CH$_2$—CH—(CH$_3$)$_2$ | —COCH$_3$ | 1 | H |
| —CH$_2$—CH—(CH$_3$)$_2$ | —COCCl$_3$ | 1 | H |
| —CH$_2$—CH—(CH$_3$)$_2$ | —CH(OH)CCl$_3$ | 1 | H |
| —CH$_2$—CH—(CH$_3$)$_2$ | —COOC$_2$H$_5$ | 1 | H |
| —CH$_2$—CH—(CH$_3$)$_2$ | —COO-Phenyl | 1 | H |
| —CH$_2$—CH—(CH$_3$)$_2$ | —S-Phenyl | 1 | H |
| —CH$_2$—CH—(CH$_3$)$_2$ | —CH$_2$—S-Phenyl | 1 | H |
| —CH$_2$—CH—(CH$_3$)$_2$ | —CO-Phenyl | 1 | H |
| —CH$_2$—CH—(CH$_3$)$_2$ | -Phenyl | 1 | H |
| —CH$_2$—CH—(CH$_3$)$_2$ | —S—(CH$_2$)$_3$CH$_3$ | 1 | H |
| —CH$_2$—CH=CH$_2$ | H | 1 | CH(CH$_3$)$_2$ |
| —CH$_2$—CH=CH$_2$ | —CH$_3$ | 1 | H |
| —CH$_2$—CH=CH$_2$ | —CF$_3$ | 1 | H |
| —CH$_2$—CH=CH$_2$ | —Cl | 1 | H |
| —CH$_2$—CH=CH$_2$ | —COCH$_3$ | 1 | H |
| —CH$_2$—CH=CH$_2$ | —COCCl$_3$ | 1 | H |
| —CH$_2$—CH=CH$_2$ | —CH(OH)CCl$_3$ | 1 | H |
| —CH$_2$—CH=CH$_2$ | —COOC$_2$H$_5$ | 1 | H |
| —CH$_2$—CH=CH$_2$ | —COO-Phenyl | 1 | H |
| —CH$_2$—CH=CH$_2$ | —S-Phenyl | 1 | H |
| —CH$_2$—CH=CH$_2$ | —CH$_2$—S-Phenyl | 1 | H |
| —CH$_2$—CH=CH$_2$ | —CO-Phenyl | 1 | H |
| —CH$_2$—CH=CH$_2$ | -Phenyl | 1 | H |
| —CH$_2$—CH=CH$_2$ | —S—(CH$_2$)$_3$CH$_3$ | 1 | H |
| —CH$_2$C≡CH | H | 1 | CH$_3$ |
| —CH$_2$C≡CH | H | 1 | C$_2$H$_5$ |
| —CH$_2$C≡CH | H | 1 | CH(CH$_3$)$_2$ |
| —CH$_2$C≡CH | —CH$_3$ | 1 | H |
| —CH$_2$C≡CH | —CF$_3$ | 1 | H |
| —CH$_2$C≡CH | —Cl | 1 | H |
| —CH$_2$C≡CH | —COCH$_3$ | 1 | H |
| —CH$_2$C≡CH | —COCCl$_3$ | 1 | H |
| —CH$_2$C≡CH | —CH(OH)CCl$_3$ | 1 | H |
| —CH$_2$C≡CH | —COOC$_2$H$_5$ | 1 | H |
| —CH$_2$C≡CH | —COO-Phenyl | 1 | H |
| —CH$_2$C≡CH | —S-Phenyl | 1 | H |
| —CH$_2$C≡CH | —CH$_2$—S-Phenyl | 1 | H |
| —CH$_2$C≡CH | —CO-Phenyl | 1 | H |
| —CH$_2$C≡CH | -Phenyl | 1 | H |
| —CH$_2$C≡CH | —S—(CH$_2$)$_3$CH$_3$ | 1 | H |
| —CH$_2$—CF$_2$Br | H | 1 | CH$_3$ |
| —CH$_2$—CF$_2$Br | H | 1 | C$_2$H$_5$ |
| —CH$_2$—CF$_2$Br | H | 1 | CH(CH$_3$)$_2$ |
| —CH$_2$—CF$_2$Br | —CH$_3$ | 1 | H |
| —CH$_2$—CF$_2$Br | —CF$_3$ | 1 | H |
| —CH$_2$—CF$_2$Br | —Cl | 1 | H |
| —CH$_2$—CF$_2$Br | —COCH$_3$ | 1 | H |
| —CH$_2$—CF$_2$Br | —COCCl$_3$ | 1 | H |
| —CH$_2$—CF$_2$Br | —CH(OH)CCl$_3$ | 1 | H |
| —CH$_2$—CF$_2$Br | —COOC$_2$H$_5$ | 1 | H |
| —CH$_2$—CF$_2$Br | —COO-Phenyl | 1 | H |
| —CH$_2$—CF$_2$Br | —S-Phenyl | 1 | H |
| —CH$_2$—CF$_2$Br | —CH$_2$—S-Phenyl | 1 | H |
| —CH$_2$—CF$_2$Br | —CO-Phenyl | 1 | H |
| —CH$_2$—CF$_2$Br | -Phenyl | 1 | H |
| —CH$_2$—CF$_2$Br | —S—(CH$_2$)$_3$CH$_3$ | 1 | H |
| —CH$_2$—C(Cl)=CH$_2$ | H | 1 | C$_2$H$_5$ |
| —CH$_2$—C(Cl)=CH$_2$ | H | 1 | CH(CH$_3$)$_2$ |
| —CH$_2$—C(Cl)=CH$_2$ | —CH$_3$ | 1 | H |
| —CH$_2$—C(Cl)=CH$_2$ | —CF$_3$ | 1 | H |
| —CH$_2$—C(Cl)=CH$_2$ | —Cl | 1 | H |
| —CH$_2$—C(Cl)=CH$_2$ | —COCH$_3$ | 1 | H |
| —CH$_2$—C(Cl)=CH$_2$ | —COCCl$_3$ | 1 | H |
| —CH$_2$—C(Cl)=CH$_2$ | —CH(OH)CCl$_3$ | 1 | H |
| —CH$_2$—C(Cl)=CH$_2$ | —COOC$_2$H$_5$ | 1 | H |
| —CH$_2$—C(Cl)=CH$_2$ | —COO-Phenyl | 1 | H |
| —CH$_2$—C(Cl)=CH$_2$ | —S-Phenyl | 1 | H |
| —CH$_2$—C(Cl)=CH$_2$ | —CH$_2$—S-Phenyl | 1 | H |
| —CH$_2$—C(Cl)=CH$_2$ | —CO-Phenyl | 1 | H |
| —CH$_2$—C(Cl)=CH$_2$ | -Phenyl | 1 | H |

TABLE-continued

| R¹ | X | n | R² |
|---|---|---|---|
| —CH$_2$—C(Cl)=CH$_2$ | —S—(CH$_2$)$_3$CH$_3$ | 1 | H |
| —CH$_2$-Cyclopropyl | H | 1 | CH$_3$ |
| —CH$_2$-Cyclopropyl | H | 1 | C$_2$H$_5$ |
| —CH$_2$-Cyclopropyl | H | 1 | CH(CH$_3$)$_2$ |
| —CH$_2$-Cyclopropyl | —CH$_3$ | 1 | H |
| —CH$_2$-Cyclopropyl | —CF$_3$ | 1 | H |
| —CH$_2$-Cyclopropyl | —Cl | 1 | H |
| —CH$_2$-Cyclopropyl | —COCH$_3$ | 1 | H |
| —CH$_2$-Cyclopropyl | —COCCl$_3$ | 1 | H |
| —CH$_2$-Cyclopropyl | —CH(OH)CCl$_3$ | 1 | H |
| —CH$_2$-Cyclopropyl | —COOC$_2$H$_5$ | 1 | H |
| —CH$_2$-Cyclopropyl | —COO-Phenyl | 1 | H |
| —CH$_2$-Cyclopropyl | —S-Phenyl | 1 | H |
| —CH$_2$-Cyclopropyl | —CH$_2$—S-Phenyl | 1 | H |
| —CH$_2$-Cyclopropyl | —CO-Phenyl | 1 | H |
| —CH$_2$-Cyclopropyl | -Phenyl | 1 | H |
| —CH$_2$-Cyclopropyl | —S—(CH$_2$)$_3$CH$_3$ | 1 | H |
| —CH$_2$—CH$_2$—OC$_2$H$_5$ | H | 1 | C$_2$H$_5$ |
| —CH$_2$—CH$_2$—OC$_2$H$_5$ | H | 1 | CH(CH$_3$)$_2$ |
| —CH$_2$—CH$_2$—OC$_2$H$_5$ | —CH$_3$ | 1 | H |
| —CH$_2$—CH$_2$—OC$_2$H$_5$ | —CF$_3$ | 1 | H |
| —CH$_2$—CH$_2$—OC$_2$H$_5$ | —Cl | 1 | H |
| —CH$_2$—CH$_2$—OC$_2$H$_5$ | —COCH$_3$ | 1 | H |
| —CH$_2$—CH$_2$—OC$_2$H$_5$ | —COCCl$_3$ | 1 | H |
| —CH$_2$—CH$_2$—OC$_2$H$_5$ | —CH(OH)CCl$_3$ | 1 | H |
| —CH$_2$—CH$_2$—OC$_2$H$_5$ | —COOC$_2$H$_5$ | 1 | H |
| —CH$_2$—CH$_2$—OC$_2$H$_5$ | —COO-Phenyl | 1 | H |
| —CH$_2$—CH$_2$—OC$_2$H$_5$ | —S-Phenyl | 1 | H |
| —CH$_2$—CH$_2$—OC$_2$H$_5$ | —CH$_2$—S-Phenyl | 1 | H |
| —CH$_2$—CH$_2$—OC$_2$H$_5$ | —CO-Phenyl | 1 | H |
| —CH$_2$—CH$_2$—OC$_2$H$_5$ | -Phenyl | 1 | H |
| —CH$_2$—CH$_2$—OC$_2$H$_5$ | —S—(CH$_2$)$_3$CH$_3$ | 1 | H |
| —CH$_2$—CH$_2$—O—CH$_2$CH$_2$Cl | H | 1 | CH$_3$ |
| —CH$_2$—CH$_2$—O—CH$_2$CH$_2$Cl | H | 1 | C$_2$H$_5$ |
| —CH$_2$—CH$_2$—O—CH$_2$CH$_2$Cl | H | 1 | CH(CH$_3$)$_2$ |
| —CH$_2$—CH$_2$—O—CH$_2$CH$_2$Cl | —CH$_3$ | 1 | H |
| —CH$_2$—CH$_2$—O—CH$_2$CH$_2$Cl | —CF$_3$ | 1 | H |
| —CH$_2$—CH$_2$—O—CH$_2$CH$_2$Cl | —Cl | 1 | H |
| —CH$_2$—CH$_2$—O—CH$_2$CH$_2$Cl | —COCH$_3$ | 1 | H |
| —CH$_2$—CH$_2$—O—CH$_2$CH$_2$Cl | —COCCl$_3$ | 1 | H |
| —CH$_2$—CH$_2$—O—CH$_2$CH$_2$Cl | —CH(OH)CCl$_3$ | 1 | H |
| —CH$_2$—CH$_2$—O—CH$_2$CH$_2$Cl | —COOC$_2$H$_5$ | 1 | H |
| —CH$_2$—CH$_2$—O—CH$_2$CH$_2$Cl | —COO-Phenyl | 1 | H |
| —CH$_2$—CH$_2$—O—CH$_2$CH$_2$Cl | —S-Phenyl | 1 | H |
| —CH$_2$—CH$_2$—O—CH$_2$CH$_2$Cl | —CH$_2$—S-Phenyl | 1 | H |
| —CH$_2$—CH$_2$—O—CH$_2$CH$_2$Cl | —CO-Phenyl | 1 | H |
| —CH$_2$—CH$_2$—O—CH$_2$CH$_2$Cl | -Phenyl | 1 | H |
| —CH$_2$—CH$_2$—O—CH$_2$CH$_2$Cl | —S—(CH$_2$)$_3$CH$_3$ | 1 | H |
| —CH$_2$—CH$_2$—N(CH$_3$)$_2$ | H | 1 | CH$_3$ |
| —CH$_2$—CH$_2$—N(CH$_3$)$_2$ | H | 1 | C$_2$H$_5$ |
| —CH$_2$—CH$_2$—N(CH$_3$)$_2$ | H | 1 | CH(CH$_3$)$_2$ |
| —CH$_2$—CH$_2$—N(CH$_3$)$_2$ | —CH$_3$ | 1 | H |
| —CH$_2$—CH$_2$—N(CH$_3$)$_2$ | —CF$_3$ | 1 | H |
| —CH$_2$—CH$_2$—N(CH$_3$)$_2$ | —Cl | 1 | H |
| —CH$_2$—CH$_2$—N(CH$_3$)$_2$ | —COCH$_3$ | 1 | H |
| —CH$_2$—CH$_2$—N(CH$_3$)$_2$ | —COCCl$_3$ | 1 | H |
| —CH$_2$—CH$_2$—N(CH$_3$)$_2$ | —CH(OH)CCl$_3$ | 1 | H |
| —CH$_2$—CH$_2$—N(CH$_3$)$_2$ | —COOC$_2$H$_5$ | 1 | H |
| —CH$_2$—CH$_2$—N(CH$_3$)$_2$ | —COO-Phenyl | 1 | H |
| —CH$_2$—CH$_2$—N(CH$_3$)$_2$ | —S-Phenyl | 1 | H |
| —CH$_2$—CH$_2$—N(CH$_3$)$_2$ | —CH$_2$—S-Phenyl | 1 | H |
| —CH$_2$—CH$_2$—N(CH$_3$)$_2$ | —CO-Phenyl | 1 | H |
| —CH$_2$—CH$_2$—N(CH$_3$)$_2$ | -Phenyl | 1 | H |
| —CH$_2$—CH$_2$—N(CH$_3$)$_2$ | —S—(CH$_2$)$_3$CH$_3$ | 1 | H |
| —CH$_2$—CH$_2$—S—CH$_3$ | H | 1 | CH$_3$ |
| —CH$_2$—CH$_2$—S—CH$_3$ | H | 1 | C$_2$H$_5$ |
| —CH$_2$—CH$_2$—S—CH$_3$ | H | 1 | CH(CH$_3$)$_2$ |
| —CH$_2$—CH$_2$—S—CH$_3$ | —CH$_3$ | 1 | H |
| —CH$_2$—CH$_2$—S—CH$_3$ | —CF$_3$ | 1 | H |
| —CH$_2$—CH$_2$—S—CH$_3$ | —Cl | 1 | H |
| —CH$_2$—CH$_2$—S—CH$_3$ | —COCH$_3$ | 1 | H |
| —CH$_2$—CH$_2$—S—CH$_3$ | —COCCl$_3$ | 1 | H |
| —CH$_2$—CH$_2$—S—CH$_3$ | —CH(OH)CCl$_3$ | 1 | H |
| —CH$_2$—CH$_2$—S—CH$_3$ | —COOC$_2$H$_5$ | 1 | H |
| —CH$_2$—CH$_2$—S—CH$_3$ | —COO-Phenyl | 1 | H |
| —CH$_2$—CH$_2$—S—CH$_3$ | —S-Phenyl | 1 | H |
| —CH$_2$—CH$_2$—S—CH$_3$ | —CH$_2$—S-Phenyl | 1 | H |
| —CH$_2$—CH$_2$—S—CH$_3$ | —CO-Phenyl | 1 | H |
| —CH$_2$—CH$_2$—S—CH$_3$ | -Phenyl | 1 | H |
| —CH$_2$—CH$_2$—S—CH$_3$ | —S—(CH$_2$)$_3$CH$_3$ | 1 | H |
| —CH$_2$—CH$_2$—S—CH$_2$F | H | 1 | CH$_3$ |

TABLE-continued

| R¹ | X | n | R² |
|---|---|---|---|
| —CH₂—CH₂—S—CH₂F | H | 1 | C₂H₅ |
| —CH₂—CH₂—S—CH₂F | H | 1 | CH(CH₃)₂ |
| —CH₂—CH₂—S—CH₂F | —CH₃ | 1 | H |
| —CH₂—CH₂—S—CH₂F | —CF₃ | 1 | H |
| —CH₂—CH₂—S—CH₂F | —Cl | 1 | H |
| —CH₂—CH₂—S—CH₂F | —COCH₃ | 1 | H |
| —CH₂—CH₂—S—CH₂F | —COCCl₃ | 1 | H |
| —CH₂—CH₂—S—CH₂F | —CH(OH)CCl₃ | 1 | H |
| —CH₂—CH₂—S—CH₂F | —COOC₂H₅ | 1 | H |
| —CH₂—CH₂—S—CH₂F | —COO-Phenyl | 1 | H |
| —CH₂—CH₂—S—CH₂F | —S-Phenyl | 1 | H |
| —CH₂—CH₂—S—CH₂F | —CH₂—S-Phenyl | 1 | H |
| —CH₂—CH₂—S—CH₂F | —CO-Phenyl | 1 | H |
| —CH₂—CH₂—S—CH₂F | -Phenyl | 1 | H |
| —CH₂—CH₂—S—CH₂F | —S—(CH₂)₃CH₃ | 1 | H |
| —CH₂-Phenyl | H | 1 | CH₃ |
| —CH₂-Phenyl | H | 1 | C₂H₅ |
| —CH₂-Phenyl | H | 1 | CH(CH₃)₂ |
| —CH₂-Phenyl | —CH₃ | 1 | H |
| —CH₂-Phenyl | —CF₃ | 1 | H |
| —CH₂-Phenyl | —Cl | 1 | H |
| —CH₂-Phenyl | —COCH₃ | 1 | H |
| —CH₂-Phenyl | —COCCl₃ | 1 | H |
| —CH₂-Phenyl | —CH(OH)CCl₃ | 1 | H |
| —CH₂-Phenyl | —COOC₂H₅ | 1 | H |
| —CH₂-Phenyl | —COO-Phenyl | 1 | H |
| —CH₂-Phenyl | —S-Phenyl | 1 | H |
| —CH₂-Phenyl | —CH₂—S-Phenyl | 1 | H |
| —CH₂-Phenyl | —CO-Phenyl | 1 | H |
| —CH₂-Phenyl | -Phenyl | 1 | H |
| —CH₂-Phenyl | —S—(CH₂)₃CH₃ | 1 | H |
| —CH₂—[4-Cl-Phenyl] | H | 1 | CH₃ |
| —CH₂—[4-Cl-Phenyl] | H | 1 | C₂H₅ |
| —CH₂—[4-Cl-Phenyl] | H | 1 | CH(CH₃)₂ |
| —CH₂—[4-Cl-Phenyl] | —CH₃ | 1 | H |
| —CH₂—[4-Cl-Phenyl] | —CF₃ | 1 | H |
| —CH₂—[4-Cl-Phenyl] | —Cl | 1 | H |
| —CH₂—[4-Cl-Phenyl] | —COCH₃ | 1 | H |
| —CH₂—[4-Cl-Phenyl] | —COCCl₃ | 1 | H |
| —CH₂—[4-Cl-Phenyl] | —CH(OH)CCl₃ | 1 | H |
| —CH₂—[4-Cl-Phenyl] | —COOC₂H₅ | 1 | H |
| —CH₂—[4-Cl-Phenyl] | —COO-Phenyl | 1 | H |
| —CH₂—[4-Cl-Phenyl] | —S-Phenyl | 1 | H |
| —CH₂—[4-Cl-Phenyl] | —CH₂—S-Phenyl | 1 | H |
| —CH₂—[4-Cl-Phenyl] | —CO-Phenyl | 1 | H |
| —CH₂—[4-Cl-Phenyl] | -Phenyl | 1 | H |
| —CH₂—[4-Cl-Phenyl] | —S—(CH₂)₃CH₃ | 1 | H |
| —CH₂—CH=CH—CH₂—[4-F-Phenyl] | H | 1 | CH₃ |
| —CH₂—CH=CH—CH₂—[4-F-Phenyl] | H | 1 | C₂H₅ |
| —CH₂—CH=CH—CH₂—[4-F-Phenyl] | H | 1 | CH(CH₃)₂ |
| —CH₂—CH=CH—CH₂—[4-F-Phenyl] | —CH₃ | 1 | H |
| —CH₂—CH=CH—CH₂—[4-F-Phenyl] | —CF₃ | 1 | H |
| —CH₂—CH=CH—CH₂—[4-F-Phenyl] | —Cl | 1 | H |
| —CH₂—CH=CH—CH₂—[4-F-Phenyl] | —COCH₃ | 1 | H |
| —CH₂—CH=CH—CH₂—[4-F-Phenyl] | —COCCl₃ | 1 | H |
| —CH₂—CH=CH—CH₂—[4-F-Phenyl] | —CH(OH)CCl₃ | 1 | H |
| —CH₂—CH=CH—CH₂—[4-F-Phenyl] | —COOC₂H₅ | 1 | H |
| —CH₂—CH=CH—CH₂—[4-F-Phenyl] | —COO-Phenyl | 1 | H |
| —CH₂—CH=CH—CH₂—[4-F-Phenyl] | —S-Phenyl | 1 | H |
| —CH₂—CH=CH—CH₂—[4-F-Phenyl] | —CH₂—S-Phenyl | 1 | H |
| —CH₂—CH=CH—CH₂—[4-F-Phenyl] | —CO-Phenyl | 1 | H |
| —CH₂—CH=CH—CH₂—[4-F-Phenyl] | -Phenyl | 1 | H |
| —CH₂—CH=CH—CH₂—[4-F-Phenyl] | —S—(CH₂)₃CH₃ | 1 | H |
| —CH₂—(CH₂)₂—O-Phenyl | H | 1 | CH₃ |
| —CH₂—(CH₂)₂—O-Phenyl | H | 1 | C₂H₅ |
| —CH₂—(CH₂)₂—O-Phenyl | H | 1 | CH(CH₃)₂ |
| —CH₂—(CH₂)₂—O-Phenyl | —CH₃ | 1 | H |
| —CH₂—(CH₂)₂—O-Phenyl | —CF₃ | 1 | H |
| —CH₂—(CH₂)₂—O-Phenyl | —Cl | 1 | H |
| —CH₂—(CH₂)₂—O-Phenyl | —COCH₃ | 1 | H |
| —CH₂—(CH₂)₂—O-Phenyl | —COCCl₃ | 1 | H |
| —CH₂—(CH₂)₂—O-Phenyl | —CH(OH)CCl₃ | 1 | H |
| —CH₂—(CH₂)₂—O-Phenyl | —COOC₂H₅ | 1 | H |
| —CH₂—(CH₂)₂—O-Phenyl | —COO-Phenyl | 1 | H |
| —CH₂—(CH₂)₂—O-Phenyl | —S-Phenyl | 1 | H |
| —CH₂—(CH₂)₂—O-Phenyl | —CH₂—S-Phenyl | 1 | H |
| —CH₂—(CH₂)₂—O-Phenyl | —CO-Phenyl | 1 | H |
| —CH₂—(CH₂)₂—O-Phenyl | -Phenyl | 1 | H |
| —CH₂—(CH₂)₂—O-Phenyl | —S—(CH₂)₃CH₃ | 1 | H |

TABLE-continued

| R¹ | | X | n | R² |
|---|---|---|---|---|
| −CH₂− (isoxazoline with CH(CH₃)₂) | | H | 1 | CH₃ |
| −CH₂− (isoxazoline with CH(CH₃)₂) | | H | 1 | C₃H₅ |
| −CH₂− (isoxazoline with CH(CH₃)₂) | | H | 1 | CH(CH₃)₂ |
| −CH₂− (isoxazoline with CH(CH₃)₂) | | −CH₃ | 1 | H |
| −CH₂− (isoxazoline with CH(CH₃)₂) | | −CF₃ | 1 | H |
| −CH₂− (isoxazoline with CH(CH₃)₂) | | −Cl | 1 | H |
| −CH₂− (isoxazoline with CH(CH₃)₂) | | −COCH₃ | 1 | H |
| −CH₂− (isoxazoline with CH(CH₃)₂) | | −COCCl₃ | 1 | H |
| −CH₂− (isoxazoline with CH(CH₃)₂) | | −CH(OH)CCl₃ | 1 | H |
| −CH₂− (isoxazoline with CH(CH₃)₂) | | −COOC₂H₅ | 1 | H |
| −CH₂− (isoxazoline with CH(CH₃)₂) | | −COO-Phenyl | 1 | H |
| −CH₂− (isoxazoline with CH(CH₃)₂) | | −S-Phenyl | 1 | H |
| −CH₂− (isoxazoline with CH(CH₃)₂) | | −CH₂−S-Phenyl | 1 | H |
| −CH₂− (isoxazoline with CH(CH₃)₂) | | −CO-Phenyl | 1 | H |

TABLE-continued

| R¹ | X | n | R² |
|---|---|---|---|
| -CH₂-[isoxazole with CH(CH₃)₂] | -Phenyl | 1 | H |
| -CH₂-[isoxazole with CH(CH₃)₂] | -S-(CH₂)₃CH₃ | 1 | H |
| -CH₂-[3,4-dichlorothiophene] | H | 1 | CH₃ |
| -CH₂-[3,4-dichlorothiophene] | H | 1 | C₂H₅ |
| -CH₂-[3,4-dichlorothiophene] | H | 1 | CH(CH₃)₂ |
| -CH₂-[3,4-dichlorothiophene] | -CH₃ | 1 | H |
| -CH₂-[3,4-dichlorothiophene] | -CF₃ | 1 | H |
| -CH₂-[3,4-dichlorothiophene] | -Cl | 1 | H |
| -CH₂-[3,4-dichlorothiophene] | -COCH₃ | 1 | H |
| -CH₂-[3,4-dichlorothiophene] | -COCCl₃ | 1 | H |
| -CH₂-[3,4-dichlorothiophene] | -CH(OH)CCl₃ | 1 | H |
| -CH₂-[3,4-dichlorothiophene] | -COOC₂H₅ | 1 | H |
| -CH₂-[3,4-dichlorothiophene] | -COO-Phenyl | 1 | H |
| -CH₂-[3,4-dichlorothiophene] | -S-Phenyl | 1 | H |

TABLE-continued
| R¹ | X | n | R² |
|---|---|---|---|
| 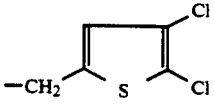 | —CH₂—S-Phenyl | 1 | H |
| 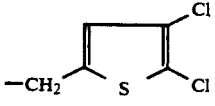 | —CO-Phenyl | 1 | H |
| 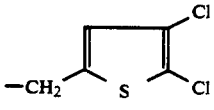 | -Phenyl | 1 | H |
| 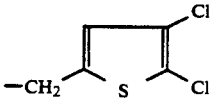 | —S—(CH₂)₃CH₃ | 1 | H |
| 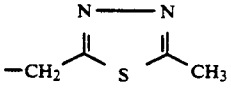 | H | 1 | CH₃ |
| 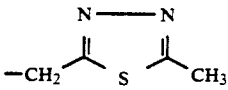 | H | 1 | C₂H₅ |
| 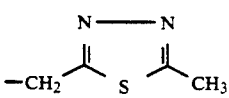 | H | 1 | CH(CH₃)₂ |
| 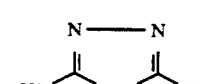 | —CH₃ | 1 | H |
| 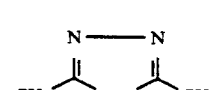 | —CF₃ | 1 | H |
| 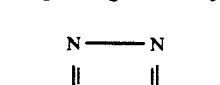 | —Cl | 1 | H |
| 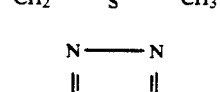 | —COCH₃ | 1 | H |
| 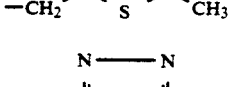 | —COCCl₃ | 1 | H |
| 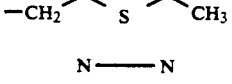 | —CH(OH)CCl₃ | 1 | H |
| 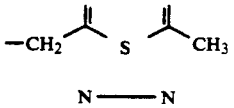 | —COOC₂H₅ | 1 | H |
| 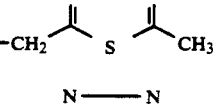 | —COO-Phenyl | 1 | H |

| R¹ | X | n | R² |
|---|---|---|---|
| 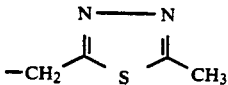 | —S-Phenyl | 1 | H |
| 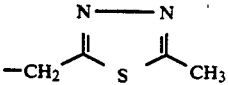 | —CH₂—2-Phenyl | 1 | H |
| 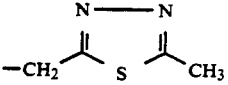 | —CO-Phenyl | 1 | H |
| 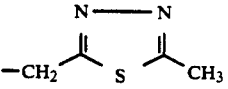 | -Phenyl | 1 | H |
| 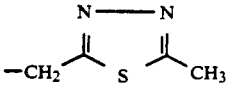 | —S—(CH₂)₃CH₃ | 1 | H |
| 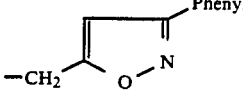 | H | 1 | CH₃ |
| 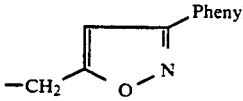 | H | 1 | C₂H₅ |
| 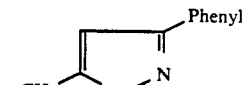 | H | 1 | CH(CH₃)₂ |
|  | —CH₃ | 1 | H |
|  | —CF₃ | 1 | H |
|  | —Cl | 1 | H |
|  | —COCH₃ | 1 | H |
| 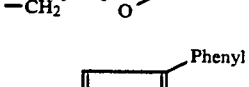 | —COCCl₃ | 1 | H |
|  | —CH(OH)CCl₃ | 1 | H |

TABLE-continued

| R¹ | X | n | R² |
|---|---|---|---|
| -CH₂-[3-phenyl-isoxazol-5-yl] | —COOC₂H₅ | 1 | H |
| -CH₂-[3-phenyl-isoxazol-5-yl] | —COO-Phenyl | 1 | H |
| -CH₂-[3-phenyl-isoxazol-5-yl] | —S-Phenyl | 1 | H |
| -CH₂-[3-phenyl-isoxazol-5-yl] | —CH₂—S-Phenyl | 1 | H |
| -CH₂-[3-phenyl-isoxazol-5-yl] | —CO-Phenyl | 1 | H |
| -CH₂-[3-phenyl-isoxazol-5-yl] | -Phenyl | 1 | H |
| -CH₂-[3-phenyl-isoxazol-5-yl] | —S—(CH₂)₃CH₃ | 1 | H |
| -CH₂-[2-methyl-5-ethoxy-oxazol-4-yl] | H | 1 | CH₃ |
| -CH₂-[2-methyl-5-ethoxy-oxazol-4-yl] | H | 1 | C₂H₅ |
| -CH₂-[2-methyl-5-ethoxy-oxazol-4-yl] | H | 1 | CH(CH₃)₂ |
| -CH₂-[2-methyl-5-ethoxy-oxazol-4-yl] | —CH₃ | 1 | H |
| -CH₂-[2-methyl-5-ethoxy-oxazol-4-yl] | —CF₃ | 1 | H |
| -CH₂-[2-methyl-5-ethoxy-oxazol-4-yl] | —Cl | 1 | H |
| -CH₂-[2-methyl-5-ethoxy-oxazol-4-yl] | —COCH₃ | 1 | H |

TABLE-continued

| R¹ | X | n | R² |
|---|---|---|---|
| -CH₂-C(=N-)-O-C(=)(O-CH₂CH₃) [oxazoline w/ OEt] | -COCCl₃ | 1 | H |
| -CH₂-C(=N-)-O-C(=)(O-CH₂CH₃) | -CH(OH)CCl₃ | 1 | H |
| -CH₂-C(=N-)-O-C(=)(O-CH₂CH₃) | -COOC₂H₅ | 1 | H |
| -CH₂-C(=N-)-O-C(=)(O-CH₂CH₃) | -COO-Phenyl | 1 | H |
| -CH₂-C(=N-)-O-C(=)(O-CH₂CH₃) | -S-Phenyl | 1 | H |
| -CH₂-C(=N-)-O-C(=)(O-CH₂CH₃) | -CH₂-S-Phenyl | 1 | H |
| -CH₂-C(=N-)-O-C(=)(O-CH₂CH₃) | -CO-Phenyl | 1 | H |
| -CH₂-C(=N-)-O-C(=)(O-CH₂CH₃) | -Phenyl | 1 | H |
| -CH₂-C(=N-)-O-C(=)(O-CH₂CH₃) | -S-(CH₂)₃CH₃ | 1 | H |
| -CH₂-C(=)(S-)-C(=N-)-Cl [thiazoline] | H | 1 | CH₃ |
| -CH₂-C(=)(S-)-C(=N-)-Cl | H | 1 | C₂H₅ |
| -CH₂-C(=)(S-)-C(=N-)-Cl | H | 1 | CH(CH₃)₂ |
| -CH₂-C(=)(S-)-C(=N-)-Cl | -CH₃ | 1 | H |
| -CH₂-C(=)(S-)-C(=N-)-Cl | -CF₃ | 1 | H |
| -CH₂-C(=)(S-)-C(=N-)-Cl | -Cl | 1 | H |

TABLE-continued
| R¹ | X | n | R² |
|---|---|---|---|
| 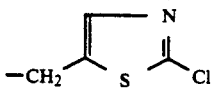 | —COCH₃ | 1 | H |
| 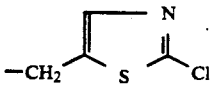 | —COCCl₃ | 1 | H |
| 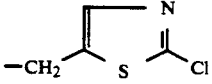 | —CH(OH)CCl₃ | 1 | H |
| 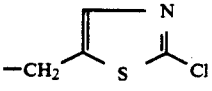 | —COOC₂H₅ | 1 | H |
| 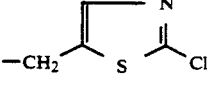 | —COO-Phenyl | 1 | H |
| 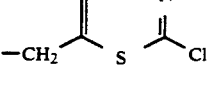 | —S-Phenyl | 1 | H |
| 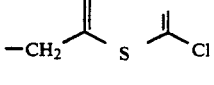 | —CH₂—S-Phenyl | 1 | H |
| 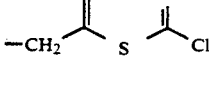 | —CO-Phenyl | 1 | H |
| 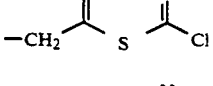 | -Phenyl | 1 | H |
| 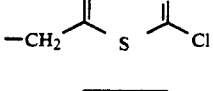 | —S—(CH₂)₃CH₃ | 1 | H |
| 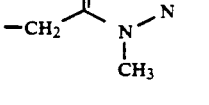 | H | 1 | CH₃ |
| 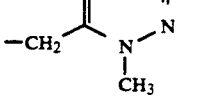 | H | 1 | C₂H₅ |
| 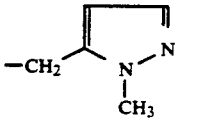 | H | 1 | CH(CH₃)₂ |
| 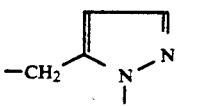 | —CH₃ | 1 | H |

| R¹ | X | n | R² |
|---|---|---|---|
| -CH₂-(1-methylpyrazol-5-yl) | -CF₃ | 1 | H |
| -CH₂-(1-methylpyrazol-5-yl) | -Cl | 1 | H |
| -CH₂-(1-methylpyrazol-5-yl) | -COCH₃ | 1 | H |
| -CH₂-(1-methylpyrazol-5-yl) | -COCCl₃ | 1 | H |
| -CH₂-(1-methylpyrazol-5-yl) | -CH(OH)CCl₃ | 1 | H |
| -CH₂-(1-methylpyrazol-5-yl) | -COOC₂H₅ | 1 | H |
| -CH₂-(1-methylpyrazol-5-yl) | -COO-Phenyl | 1 | H |
| -CH₂-(1-methylpyrazol-5-yl) | -S-Phenyl | 1 | H |
| -CH₂-(1-methylpyrazol-5-yl) | -CH₂-S-Phenyl | 1 | H |
| -CH₂-(1-methylpyrazol-5-yl) | -CO-Phenyl | 1 | H |
| -CH₂-(1-methylpyrazol-5-yl) | -Phenyl | 1 | H |

TABLE-continued

| R¹ | X | n | R² |
|---|---|---|---|
| -CH₂-(1-methyl-pyrazol-5-yl) | -S-(CH₂)₃CH₃ | 1 | H |
| -CH₂-(1-methyl-pyrrol-2-yl) | H | 1 | CH₃ |
| -CH₂-(1-methyl-pyrrol-2-yl) | H | 1 | C₂H₅ |
| -CH₂-(1-methyl-pyrrol-2-yl) | H | 1 | CH(CH₃)₂ |
| -CH₂-(1-methyl-pyrrol-2-yl) | -CH₃ | 1 | H |
| -CH₂-(1-methyl-pyrrol-2-yl) | -CF₃ | 1 | H |
| -CH₂-(1-methyl-pyrrol-2-yl) | -Cl | 1 | H |
| -CH₂-(1-methyl-pyrrol-2-yl) | -COCH₃ | 1 | H |
| -CH₂-(1-methyl-pyrrol-2-yl) | -COCCl₃ | 1 | H |
| -CH₂-(1-methyl-pyrrol-2-yl) | -CH(OH)CCl₃ | 1 | H |
| -CH₂-(1-methyl-pyrrol-2-yl) | -COOC₂H₅ | 1 | H |

TABLE-continued
| R¹ | X | n | R² |
|---|---|---|---|
| 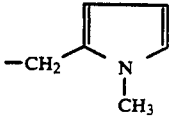 | —COO-Phenyl | 1 | H |
| 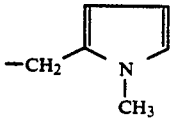 | —S-Phenyl | 1 | H |
| 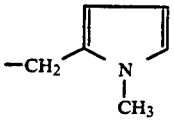 | —CH₂—S-Phenyl | 1 | H |
| 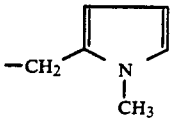 | —CO-Phenyl | 1 | H |
| 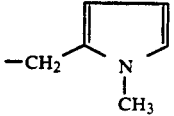 | -Phenyl | 1 | H |
| 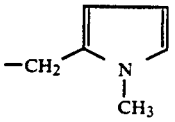 | —S—(CH₂)₃CH₃ | 1 | H |
| 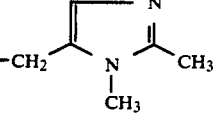 | H | 1 | CH₃ |
| 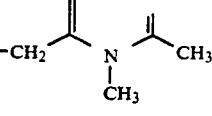 | H | 1 | C₂H₅ |
| 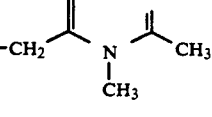 | H | 1 | CH(CH₃)₂ |
| 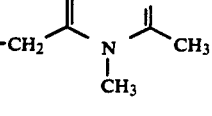 | —CH₃ | 1 | H |
| 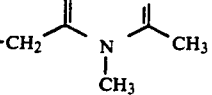 | —CF₃ | 1 | H |

TABLE-continued
| R¹ | X | n | R² |
|---|---|---|---|
| 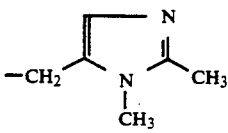 | —Cl | 1 | H |
| 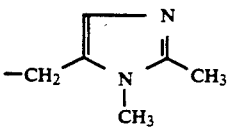 | —COCH₃ | 1 | H |
| 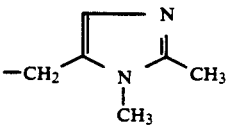 | —COCCl₃ | 1 | H |
| 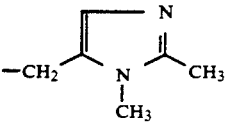 | —CH(OH)CCl₃ | 1 | H |
| 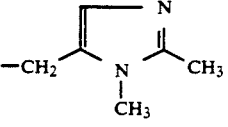 | —COOC₂H₅ | 1 | H |
| 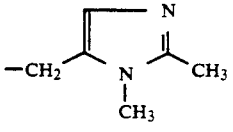 | —COO-Phenyl | 1 | H |
| 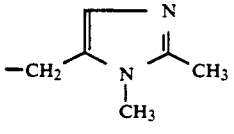 | —S-Phenyl | 1 | H |
| 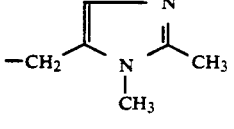 | —CH₂—S-Phenyl | 1 | H |
| 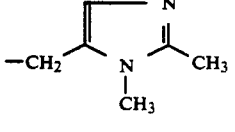 | —CO-Phenyl | 1 | H |
| 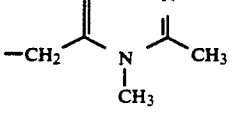 | -Phenyl | 1 | H |
| 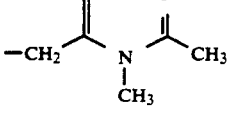 | —S—(CH₂)₃CH₃ | 1 | H |

| R¹ | X | n | R² |
|---|---|---|---|
| -CH₂-(6-chloropyridin-3-yl) | H | 1 | CH₃ |
| -CH₂-(6-chloropyridin-3-yl) | H | 1 | C₂H₅ |
| -CH₂-(6-chloropyridin-3-yl) | H | 1 | CH(CH₃)₂ |
| -CH₂-(6-chloropyridin-3-yl) | -CH₃ | 1 | H |
| -CH₂-(6-chloropyridin-3-yl) | -CF₃ | 1 | H |
| -CH₂-(6-chloropyridin-3-yl) | -Cl | 1 | H |
| -CH₂-(6-chloropyridin-3-yl) | -COCH₃ | 1 | H |
| -CH₂-(6-chloropyridin-3-yl) | -COCCl₃ | 1 | H |
| -CH₂-(6-chloropyridin-3-yl) | -CH(OH)CCl₃ | 1 | H |
| -CH₂-(6-chloropyridin-3-yl) | -COOC₂H₅ | 1 | H |
| -CH₂-(6-chloropyridin-3-yl) | -COO-Phenyl | 1 | H |
| -CH₂-(6-chloropyridin-3-yl) | -S-Phenyl | 1 | H |
| -CH₂-(6-chloropyridin-3-yl) | -CH₂-S-Phenyl | 1 | H |

TABLE-continued
| R¹ | X | n | R² |
|---|---|---|---|
| 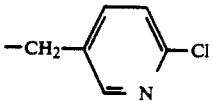 | —CO-Phenyl | 1 | H |
| 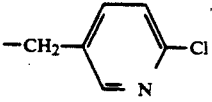 | -Phenyl | 1 | H |
| 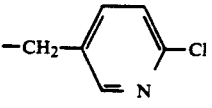 | —S—(CH$_2$)$_3$CH$_3$ | 1 | H |
| 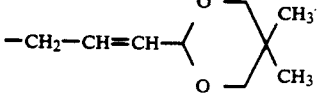 | H | 1 | CH$_3$ |
| 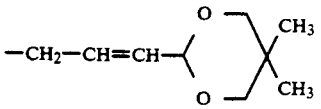 | H | 1 | C$_2$H$_5$ |
| 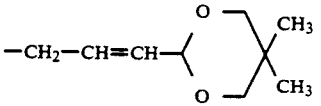 | H | 1 | CH(CH$_3$)$_2$ |
| 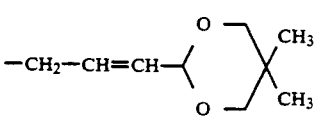 | —CH$_3$ | 1 | H |
| 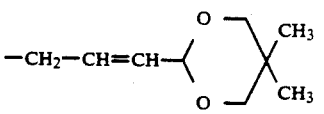 | —CF$_3$ | 1 | H |
| 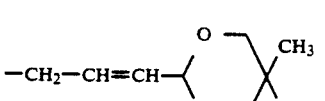 | —Cl | 1 | H |
| 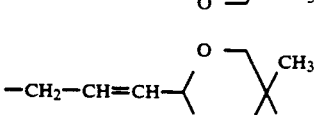 | —COCH$_3$ | 1 | H |
| 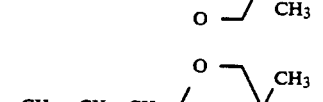 | —COCCl$_3$ | 1 | H |
| 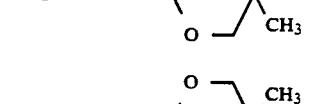 | —CH(OH)CCl$_3$ | 1 | H |
| 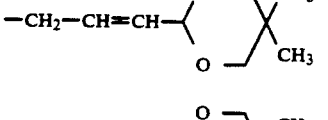 | —COOC$_2$H$_5$ | 1 | H |

TABLE-continued
| R¹ | X | n | R² |
|---|---|---|---|
| 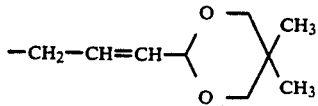 | —COO-Phenyl | 1 | H |
| 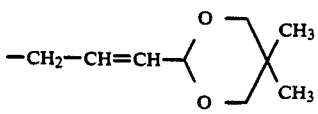 | —S-Phenyl | 1 | H |
| 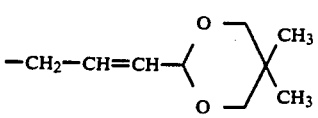 | —CH₂—S-Phenyl | 1 | H |
| 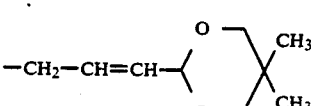 | —CO-Phenyl | 1 | H |
| 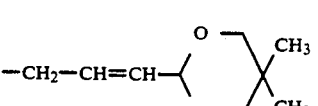 | -Phenyl | 1 | H |
| 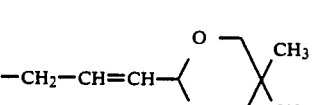 | —S—(CH₂)₃CH₃ | 1 | H |
| 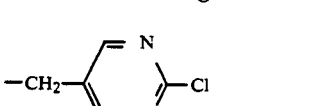 | H | 1 | CH₃ |
| 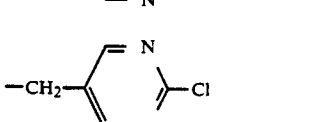 | H | 1 | C₂H₅ |
| 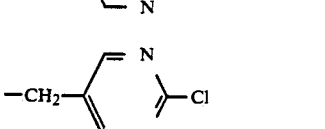 | H | 1 | CH(CH₃)₂ |
| 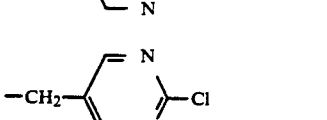 | —CH₃ | 1 | H |
| 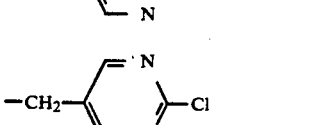 | —CF₃ | 1 | H |
| 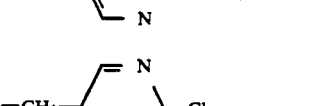 | —Cl | 1 | H |
| 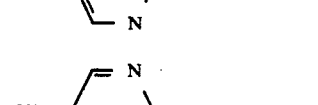 | —COCH₃ | 1 | H |

| R¹ | X | n | R² |
|---|---|---|---|
| -CH₂-(2-chloropyrimidin-5-yl) | —COCCl₃ | 1 | H |
| -CH₂-(2-chloropyrimidin-5-yl) | —CH(OH)CCl₃ | 1 | H |
| -CH₂-(2-chloropyrimidin-5-yl) | —COOC₂H₅ | 1 | H |
| -CH₂-(2-chloropyrimidin-5-yl) | —COO-Phenyl | 1 | H |
| -CH₂-(2-chloropyrimidin-5-yl) | —S-Phenyl | 1 | H |
| -CH₂-(2-chloropyrimidin-5-yl) | —CH₂—S-Phenyl | 1 | H |
| -CH₂-(2-chloropyrimidin-5-yl) | —CO-Phenyl | 1 | H |
| -CH₂-(2-chloropyrimidin-5-yl) | -Phenyl | 1 | H |
| -CH₂-(2-chloropyrimidin-5-yl) | —S—(CH₂)₃CH₃ | 1 | H |
| -CH₂-(5-trifluoromethylfuran-2-yl) | H | 1 | CH₃ |
| -CH₂-(5-trifluoromethylfuran-2-yl) | H | 1 | C₂H₅ |
| -CH₂-(5-trifluoromethylfuran-2-yl) | H | 1 | CH(CH₃)₂ |
| -CH₂-(5-trifluoromethylfuran-2-yl) | —CH₃ | 1 | H |

| R¹ | X | n | R² |
|---|---|---|---|
| 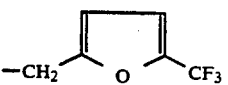 | —CF₃ | 1 | H |
| 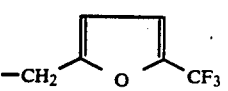 | —Cl | 1 | H |
| 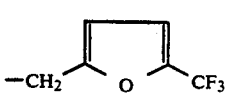 | —COCH₃ | 1 | H |
|  | —COCCl₃ | 1 | H |
| 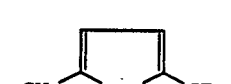 | —CH(OH)CCl₃ | 1 | H |
|  | —COOC₂H₅ | 1 | H |
|  | —COO-Phenyl | 1 | H |
| 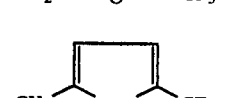 | —S-Phenyl | 1 | H |
| 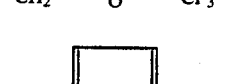 | —CH₂—S-Phenyl | 1 | H |
| 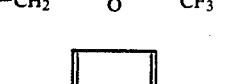 | —CO-Phenyl | 1 | H |
| 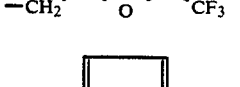 | -Phenyl | 1 | H |
| 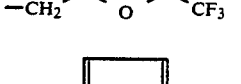 | —S—(CH₂)₃CH₃ | 1 | H |

The compounds of the formula I are suitable for effectively combating pests such as insects, arachnids and nematodes. They may be used as pesticides in crop protection and in the hygiene, stores protection and veterinary sector.

Examples of injurious insects belonging to the Lepidoptera order are Agrotis upsilon, Agrotis segetum, Alabama argillacea, Anticarsia gemmatalis, Argyresthia conjugella, Autographs gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranean Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis.

Examples from the Coleoptera order are Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria.

Examples from the Diptera order are Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa.

Examples from the Thysanoptera order are Frankliniella fusca, Frankliniella occidentalis, Frankliniella tritici, Scirtothrips citri, Thrips oryzae, Thrips palmi and Thrips tabaci.

Examples from the Hymenoptera order are Athalia rosae, Atta cephalotes, Atta sexdens, Atta texana, Hoplocampa minuta, Hoplocampa testudinea, Monomorium pharaonis, Solenopsis geminata and Solenopsis invicta.

Examples from the Heteroptera order are Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis and Thyanta perditor.

Examples from the Homoptera order are Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii.

Examples from the Isoptera order are Calotermes flavicollis, Leucotermes flavipes, Reticulitermes lucifugus and Termes natalensis.

Examples from the Orthoptera order are Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus.

Examples from the Acarina order are Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius and Tetranychus urticae.

Examples from the nematodes class are root-knot nematodes, e.g., Meloidogyne hapla, Meloidogyne incognita and Meloidogyne javanica, cyst-forming nematodes, e.g., Globodera rostochiensis, Heterodera avenae, Hetrodera glycinae, Heterodera schachtii and Heterodera trifolii, and stem and leaf eelworms, e.g., Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus and Pratylenchus goodeyi.

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

The formulations contain from 0.1 to 95, and preferably 0.5 to 90, % by weight of active ingredient. The active ingredients are used in a purity of 90 to 100, and preferably 95 to 100, % (according to the NMR spectrum).

Examples of formulations are as follows:

I. 5 parts by weight of compound no. 2 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence (active ingredient content: 23 wt %).

III. 10 parts by weight of compound no. 6 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil (active ingredient content: 9 wt %).

IV. 20 parts by weight of compound no. 1 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil (active ingredient content: 16 wt %).

V. 80 parts by weight of compound no. 5 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill (active ingredient content: 80 wt %).

VI. 90 parts by weight of compound no. 4 is mixed with 10 parts by weight of N-methyl-alpha-pyrrolidone.

A mixture is obtained which is suitable for application in the form of very fine drops (active ingredient content: 90 wt %).

VII. 20 parts by weight of compound no. 12 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and uniformly distributing ot therein, an aqueous dispersion is obtained containing 0.02 wt % of the active ingredient.

VIII. 20 parts by weight of compound no. 7 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By finely distributing the mixture in 20,000 parts by weight of water, a spray liquor is obtained containing 0.1 wt % of active ingredient.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The active ingredient concentrations in the ready-to-use formulations may vary within wide limits; generally, they are from 0.0001 to 10, and preferably from 0.01 to 1, %.

The active ingredients may also be successfully used in the ultra-low-volume (ULV) method, in which it is possible to apply formulations containing more than 95 wt % of active ingredient, or even without any additives at all.

When the active ingredients are used in the open, the amounts applied are from 0.01 to 3, and preferably from 0.05 to 1, kg/ha.

There may be added to the active ingredients (if desired, immediately before use (tankmix)) oils of various types, herbicides, fungicides, other pesticides or bactericides. These agents may be admixed in a weight ratio of from 1:10 to 10:1.

SYNTHESIS EXAMPLES

The directions given in the synthesis examples below were employed, after appropriate modifications of the starting materials, to obtain further compounds I. The compounds thus obtained are listed in the following tables with their physical data.

A. Manufacture of the Intermediates

A1. Manufacture of 1-amino-3-methoxyaminopropane dihydrochloride (II-1)

10 g (0.037 mol) of N-(3-bromophenyl)-phthalimide, 6.2 g (0.075 mol) of methoxyamine hydrochloride and 15.0 g of sodium carbonate are suspended in 150 ml of ethanol and refluxed for 12 hours. After cooling, the salts are separated off by filtration and the solvent is removed. The oil which remains is treated with ethyl acetate, the insoluble residue is separated off and the solvent is removed. The oil which remains is taken up in 25 ml of ethanol and 1.15 g (0.023 mol) of hydrazine hydrate is added. The solution is stirred for 30 minutes at 80° C. After the addition of 3 ml of concentrated hydrochloric acid the mixture is stirred for a further 30 minutes at 80° C. 10 ml of water is then added and the whole filtered. Concentration and recrystallization from ethanol give the desired product as colorless crystals.

Melting point: 155°–156° C.; yield: 1.8 g (27% of theory).

Further compounds of the formula II, obtained by the same process in the form of their hydrochlorides, are listed in the following Table A.

taken up in ethyl acetate and extracted with water. The organic phase is dried with sodium sulfate and the solvent removed. There is obtained 1-methoxy-2-methylthio-1,4,5,6-tetrahydropyrimidine (VII-1) as a slightly yellowish oil.

$^1$H-NMR (CDCl$_3$) δ 3.7 (s,3H), 3.44 (m,4H), 2.27 (s,3H), 1.96 (m,2H).

Yield: 13.9 g, 93% of theory.

2.0 g (0.013 mol) of VII-1 is heated under argon to 120° C. and 1.8 g (0.014 mol) of ethyl nitroacetate is slowly added. The mixture is stirred for 1 hour at 120° C. After the mixture has cooled, it is diluted with a mixture of ethanol and methylene chloride (4:1), and activated carbon is added. The mixture is filtered, the solvent is removed and the residue is recrystallized

TABLE A

| No. | R$^1$ | R$^2$ | Phys. data[mp. (°C.) or $^1$H-NMR] |
|---|---|---|---|
| II-1 | CH$_3$ | H | 155–156 |
| II-2 | CH$_2$CH$_3$ | H | 60 |
| II-3 | CH$_2$C$_6$H$_5$ | H | 139–140 |
| II-4 | —CH$_2$—CH=CH$_2$ | H | 94–95 |
| II-5 | —CH$_2$—(isoxazole with CH(CH$_3$)$_2$) | H | 138 |
| II-6 | —CH$_2$—(2-chloropyridyl) | H | $^1$H-NMR(DMSO)δ: 8.94(s, 1H), 8.19(bs, 3H), 8.01(d, 1H), 7.60(d, 1H), 5.30(s, 2H), 3.37 (t, 2H), 2.94(m, 2H), 2.04(m, 2H) |
| II-7 | —CH$_2$—(pyridyl) | H | $^1$H-NMR(DMSO)δ: 9.06(s, 1H), 8.94(d, 1H), 8.63(d, 1H), 8.25(bs, 3H), 8.06(t, 1H), 5.40 (s, 2H), 3.31(t, 2H), 2.92(m, 2H), 2.03(m, 2H) |
| II-8 | —CH$_2$—[4-Cl—C$_6$H$_4$] | H | 184–186 |
| II-9 | —CH$_2$—(isoxazole with C$_6$H$_5$) | H | 165–166 |
| II-10 | —CH$_2$—(CH$_2$)$_2$—O—C$_6$H$_5$ | H | $^1$H-NMR(DMSO)δ: 8.30(bs, 3H), 7.33(m, 2H), 6.97(m, 3H), 4.36(t, 2H), 4.06(t, 2H), 3.32 (t, 2H), 2.96(m, 2H), 2.09(m, 4H) |
| II-11 | —CH$_2$—[3-Cl—C$_6$H$_4$] | H | 169–170 |

B: Preparation of the Active Ingredients

EXAMPLE 1

Preparation of ethyl-2-(hexahydro-1-methoxypyrimidin-2-ylidene)-2-nitroacetate 30 g (0.29 mol) of 1-amino-3-methoxyaminopropane is slowly added to a solution of 44 g (0.58 mol) of carbon disulfide in 90 ml of ethanol, and stirred for 1 hour at room temperature. Subsequently, 7 ml of concentrated hydrochloric acid is added and the solution is refluxed for 5 hours. The hexahydro-1-methoxy-2-pyrimidinethione (VIIa-1) which precipitates out on cooling is separated off and dried under reduced pressure.

M.p.: 124° C.; yield: 22.5 g (54% of theory)

Initially, 12 g of sodium carbonate and then, slowly, 16 g (0.11 mol) of methyl iodide are added to a solution of 13.6 g (0.09 mol) of VIIa-1 in tetrahydrofuran; the mixture is refluxed for 2 hours. The salts are separated by filtration and the solvent is removed. The residue is taken up in ethyl acetate and extracted with water. The from isopropanol. The title compound is obtained as slightly yellowish crystals.

M.p.: 177°–178° C.; yield: 0.7 g, 23% of theory.

EXAMPLE 2

Preparation of hexahydro-1-methoxy-2-nitromethylenepyrimidine 2.0 g (0.011 mol) of 1-amino-3-methoxyaminopropane dihydrochloride and 2.53 g (0.023 mol) of potassium tert-butylate are refluxed in 120 ml of ethanol for 1 hour. Subsequently, 1.86 g (0.011 mol) of 1,1-bis(methylthio)-2-nitroethylene is added and the mixture is refluxed for a further 6 hours until no more gas evolves. The salts are separated off by filtration and the solvent is removed. The crude product is purified by flash chromatography using toluene/ethanol as developer. The desired product is obtained as slightly yellowish crystals.

M.p.: 84°–85° C.; yield: 1.5 g, 77% of theory.

TABLE 1

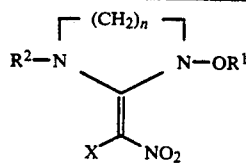

| No. | R¹ | R² | X | n | Phys. data[mp. (°C.) or ¹H-NMR] |
|---|---|---|---|---|---|
| 1 | —CH₃ | H | —COOC₂H₅ | 1 | 177–178 |
| 2 | —CH₃ | H | H | 1 | 84–85 |
| 3 | —CH₂CH₃ | H | H | 1 | 126–127 |
| 4 | —CH₃ | H | H | 0 | >200 |
| 5 | —CH₂C₆H₅ | H | H | 1 | 114 |
| 6 | —CH₂—CH=CH₂ | H | H | 1 | 110 |
| 7 | —CH₂-[isoxazoline-CH(CH₃)₂] | H | H | 1 | 98 |
| 8 | —CH₂—[3-Cl—C₆H₄] | H | H | 1 | 86–87 |
| 9 | —CH₂—[4-Cl—C₆H₄] | H | H | 1 | 165–166 |
| 10 | —CH₂-[isoxazoline-C₆H₅] | H | H | 1 | 119–120 |
| 11 | —CH₂-(3-pyridyl) | H | H | 1 | 101 |
| 12 | —CH₂-(2-Cl-pyridyl) | H | H | 1 | 158 |
| 13 | —CH₂—(CH₂)₂—O—C₆H₅ | H | H | 1 | ¹H-NMR(CDCl₃)δ: 10.19(bs, 1H), 7.29(m, 2H), 6.99–6.86(m, 4H), 4.09(m, 2H), 3.59(m, 2H), 3.38 (m, 2H), 2.12(m, 4H) |
| 14 | —CH₂ | H | —CH₂—S—[4-CH₃—C₆H₄] | 1 | 96 |
| 15 | —CH₂—[3-F—C₆H₄] | H | H | 1 | 88 |
| 16 | —CH₂—[2-F—C₆H₄] | H | H | 1 | 155 |
| 17 | —CH₂—[2,6-F—C₆H₃] | H | H | 1 | 158 |
| 18 | —CH₂—[3-CF₃—C₆H₄] | H | H | 1 | 128 |
| 19 | —CH₂—[2-Cl—C₆H₄] | H | H | 1 | 193 |

USE EXAMPLES

The insecticidal action of the compounds of the general formula I was demonstrated by the following experiments:

The active ingredients were used either
a) as a 0.1% acetonic solution or
b) as a 10% emulsion concentrate obtained by emulsifying the active ingredients in a mixture containing 70 wt % of cyclohexanone, 20 wt % of Nekanil ® LN ( Lutensol AP6, a spreader-sticker with an emulsifying and dispersing action based on ethoxylated alkylphenols) and 10 wt % of Emulphor ® EL (an emulsifier based on ethoxylated fatty alcohols).

The concentrations given in the examples were obtained by diluting the formulated active ingredients with acetone in the case of a) and with water in the case of b).

Upon conclusion of the experiments the lowest concentration was determined at which the compounds caused, compared with the untreated controls, 80 to 100% inhibition or mortality (action threshold or minimum concentration).

In contact experiments on a) Prodenia litura and b) Plutella maculipennis, compounds 2 and 3 had action thresholds of 0.1 and 0.04 mg respectively in the case of a), and 400 ppm in the case of b).

We claim:

1. A 1-alkoxy-1,3-diazacycloalkane compound of the formula I

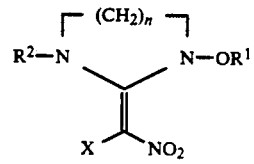

where
n is 0 or 1;

$R^1$ is unsubstituted $C_1-C_{10}$-alkyl, $C_1-C_6$-alkylcarbonyl, $C_1-C_6$-cycloalkylcarbonyl, $C_3-C_6$-alkenyl or $C_3-C_6$-alkynyl group;

X is hydrogen; halogen, $C_1-C_4$-alkoxy; $C_1-C_4$-alkylthio; $C_1-C_6$-alkylcarbonyl; $C_1-C_6$-haloalkylcarbonyl; $C_1-C_6$-alkoxycarbonyl; unsubstituted $C_1-C_4$-alkyl or $C_1-C_4$-alkyl substituted by from one to nine halogen atoms or from one to three of the following groups; hydroxyl, $C_1-C_4$-alkoxy, $C_1-C_4$-alkylthio, phenoxy and phenylthio; an unsubstituted phenyl, phenoxy, phenylthio, benzoyl or phenyloxy-carbonyl group, or one of said groups which the phenyl radicals are substituted by from one to five halogen atoms or from one to three of the following groups: cyano, nitro, $C_1-C_4$-alkyl; and $C_1-C_4$-alkoxy; and $R^2$ is hydrogen or $C_1-C_4$-alkyl.

2. A 1-alkoxy-1,3-diazacycloalkane compound of the formula I as defined in claim 1, where n is 1 and X and $R^2$ are each hydrogen.

3. A compound of the formula I as defined in claim 1, wherein $R^2$ is hydrogen.

4. A compound of the formula I as defined in claim 1, wherein X is hydrogen.

5. A compound of the formula I as defined in claim 1, wherein n is 1.

6. A compound of the formula I as defined in claim 1, wherein $R^2$ is hydrogen, X is hydrogen, and n is 1.

7. A pesticidal composition for combating insects nematodes or arachnids which comprises a carrier or diluent and an effective amount of 1-alkoxy-1,3-diazacycloalkane of the formula I as defined in claim 1.

8. A method for controlling insects arachnids and nematodes, wherein such pests or their habitat are or is treated with an effective amount of a 1-alkoxy-1,3-diazacycloalkane of the formula I as defined in claim 1.

9. A method for controlling insects, arachnids and nematodes, wherein such pests or their habitat are or is treated with an effective amount of a compound of the formula I as defined in claim 3.

10. A method for controlling insects, arachnids and nematodes, wherein such pests or their habitat are or is treated with an effective amount of a compound of the formula I as defined in claim 4.

11. A method for controlling insects, arachnids and nematodes, wherein such pests or their habitat are or is treated with an effective amount of a compound of the formula I as defined in claim 5.

12. A method for controlling insects, arachnids and nematodes, wherein such pests or their habitat are or is treated with an effective amount of a compound of the formula I as defined in claim 6.

* * * * *